(12) United States Patent
Blau

(10) Patent No.: US 10,105,168 B2
(45) Date of Patent: *Oct. 23, 2018

(54) STEREOTACTIC COMPUTER ASSISTED SURGERY BASED ON THREE-DIMENSIONAL VISUALIZATION

(75) Inventor: Arno Blau, Basel (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/812,125

(22) PCT Filed: Jan. 9, 2009

(86) PCT No.: PCT/EP2009/050210
§ 371 (c)(1),
(2), (4) Date: Sep. 17, 2010

(87) PCT Pub. No.: WO2009/087214
PCT Pub. Date: Jul. 16, 2009

(65) Prior Publication Data
US 2011/0019884 A1 Jan. 27, 2011

Related U.S. Application Data

(60) Provisional application No. 61/010,543, filed on Jan. 9, 2008.

(51) Int. Cl.
*A61B 17/74* (2006.01)
*A61B 17/17* (2006.01)
(Continued)

(52) U.S. Cl.
CPC ........ *A61B 17/744* (2013.01); *A61B 17/1703* (2013.01); *A61B 17/1721* (2013.01);
(Continued)

(58) Field of Classification Search
CPC ......... A61B 34/20; A61B 90/36; A61B 90/39; A61B 6/12; A61B 6/4007; A61B 6/4266;
(Continued)

(56) References Cited

U.S. PATENT DOCUMENTS 5,122,141 A 6/1992 Simpson et al.
5,436,542 A 7/1995 Petelin et al.
(Continued)

FOREIGN PATENT DOCUMENTS

CN 1424673 A 6/2003
CN 1203435 C 5/2005
(Continued)

OTHER PUBLICATIONS

Guoyan Zheng et al., Precise estimation of postoperative cup alignment from single standard X-ray radiograph with gonadal shielding, Proceedings of the 10th international conference on Medical image computing and computer-assisted intervention, Oct. 29-Nov. 2, 2007, Brisbane, Australia.*
(Continued)

*Primary Examiner* — Michael Kahelin
*Assistant Examiner* — Helene Bor
(74) *Attorney, Agent, or Firm* — Lerner, David, Littenberg, Krumholz & Mentlik, LLP

(57) ABSTRACT

A computer assisted surgical system that includes an apparatus (110) for imaging a region of interest of a portion of an anatomy of a subject; a memory containing executable instructions; and a processor programmed using the instructions to receive two or more two-dimensional images of the region of interest taken at different angles from the apparatus and process the two or more two-dimensional images to produce three dimensional information associated with the region of interest.

24 Claims, 29 Drawing Sheets

(51) Int. Cl.
*A61B 90/00* (2016.01)
*A61B 34/20* (2016.01)
*A61B 34/00* (2016.01)
*A61B 34/10* (2016.01)

(52) U.S. Cl.
CPC ........ *A61B 17/1725* (2013.01); *A61B 17/746* (2013.01); *A61B 90/37* (2016.02); *A61B 17/1728* (2013.01); *A61B 34/20* (2016.02); *A61B 34/25* (2016.02); *A61B 2034/107* (2016.02); *A61B 2090/363* (2016.02); *A61B 2090/367* (2016.02); *A61B 2090/376* (2016.02)

(58) Field of Classification Search
CPC .............. A61B 34/10; A61B 2034/102; A61B 2034/105; A61B 2034/108; A61B 2034/2051; A61B 2034/2055; A61B 2034/2072; A61B 34/25; A61B 2034/252; A61B 2034/254; A61B 2034/256; A61B 2034/0818; A61B 90/361; A61B 2090/364; A61B 2090/365; A61B 2090/367; A61B 2090/376; A61B 2090/3916; A61B 2090/3954; A61B 2090/3975; A61B 2090/3987; A61B 2090/502; A61B 2017/00716; A61B 2017/0268; G06Q 10/087; A61F 2/4603; A61F 2/34; A61F 2/36; A61F 2/4607; A61F 2/4609; A61F 2/461; A61F 2002/3008; A61F 2002/3067; A61F 2002/3895; A61F 2002/4632; A61F 2250/0002; A61F 2250/0098
USPC .................. 600/426, 429, 414, 242; 128/920
See application file for complete search history.

(56) References Cited

U.S. PATENT DOCUMENTS

| | | | |
|---|---|---|---|
| 5,480,402 A | 1/1996 | Kim | |
| 5,533,143 A | 7/1996 | Takeo | |
| 5,622,170 A | 4/1997 | Schulz | |
| 5,682,886 A | 11/1997 | Delp et al. | |
| 5,799,055 A | 8/1998 | Peshkin et al. | |
| 5,841,830 A | 11/1998 | Barni et al. | |
| 5,880,976 A | 3/1999 | DiGioia, III et al. | |
| 6,002,859 A | 12/1999 | DiGioia, III et al. | |
| 6,021,343 A | 2/2000 | Foley et al. | |
| 6,053,918 A | 4/2000 | Spievack | |
| 6,069,932 A | 5/2000 | Peshkin et al. | |
| 6,101,543 A | 8/2000 | Alden et al. | |
| 6,149,592 A | 11/2000 | Yanof et al. | |
| 6,198,794 B1 | 3/2001 | Peshkin et al. | |
| 6,205,411 B1 | 3/2001 | DiGioia, III et al. | |
| 6,226,548 B1 | 5/2001 | Foley et al. | |
| 6,285,902 B1 | 9/2001 | Kienzle, III et al. | |
| 6,341,231 B1* | 1/2002 | Ferre et al. ................... | 600/424 |
| 6,370,421 B1 | 4/2002 | Williams et al. | |
| 6,428,547 B1 | 8/2002 | Vilsmeier et al. | |
| 6,450,978 B1 | 9/2002 | Brosseau et al. | |
| 6,470,207 B1 | 10/2002 | Simon et al. | |
| 6,477,400 B1 | 11/2002 | Barrick | |
| 6,503,249 B1 | 1/2003 | Krause | |
| 6,510,241 B1 | 1/2003 | Vaillant et al. | |
| 6,535,756 B1 | 3/2003 | Simon et al. | |
| 6,674,883 B1 | 1/2004 | Wei et al. | |
| 6,697,664 B2 | 2/2004 | Kienzle, III et al. | |
| 6,701,174 B1 | 3/2004 | Krause et al. | |
| 6,711,432 B1 | 3/2004 | Krause et al. | |
| 6,718,194 B2 | 4/2004 | Kienzle, III | |
| 6,725,080 B2 | 4/2004 | Melkent et al. | |
| 6,747,646 B2 | 6/2004 | Gueziec et al. | |
| 6,810,280 B2 | 10/2004 | Strobel | |
| 6,856,826 B2 | 2/2005 | Seeley et al. | |
| 6,887,245 B2 | 5/2005 | Kienzle, III et al. | |
| 6,917,827 B2 | 7/2005 | Kienzle, III | |
| 6,922,581 B2 | 7/2005 | Kienzle, III | |
| 7,130,676 B2 | 10/2006 | Barrick | |
| 7,167,738 B2 | 1/2007 | Schweikard et al. | |
| 7,203,277 B2 | 4/2007 | Birkenbach et al. | |
| 7,235,076 B2 | 6/2007 | Pacheco | |
| RE40,176 E | 3/2008 | Peshkin et al. | |
| 7,392,076 B2 | 6/2008 | Moctezuma de La Barrera | |
| 7,427,200 B2 | 9/2008 | Noble et al. | |
| 7,427,272 B2 | 9/2008 | Richard et al. | |
| 7,567,834 B2 | 7/2009 | Clayton et al. | |
| 7,570,791 B2 | 8/2009 | Frank et al. | |
| 7,887,545 B2 | 2/2011 | Fernandez et al. | |
| 7,966,058 B2* | 6/2011 | Xue et al. ................... | 600/427 |
| 8,090,166 B2 | 1/2012 | Rappaport et al. | |
| 8,611,697 B2 | 12/2013 | Nathaniel et al. | |
| 9,109,998 B2 | 8/2015 | Nathaniel et al. | |
| 9,111,180 B2 | 8/2015 | Rappaport et al. | |
| 9,433,390 B2 | 9/2016 | Nathaniel et al. | |
| 2001/0036245 A1 | 11/2001 | Kienzle et al. | |
| 2002/0188194 A1 | 12/2002 | Cosman | |
| 2004/0009459 A1* | 1/2004 | Anderson et al. ............ | 434/262 |
| 2004/0030245 A1 | 2/2004 | Noble et al. | |
| 2004/0039259 A1 | 2/2004 | Krause et al. | |
| 2004/0082849 A1* | 4/2004 | Schweikard et al. ......... | 600/424 |
| 2004/0097922 A1 | 5/2004 | Mullaney | |
| 2004/0171924 A1* | 9/2004 | Mire et al. ................... | 600/407 |
| 2004/0230199 A1 | 11/2004 | Jansen et al. | |
| 2004/0243148 A1 | 12/2004 | Wasielewski | |
| 2004/0263535 A1 | 12/2004 | Birkenbach et al. | |
| 2005/0021043 A1 | 1/2005 | Jansen et al. | |
| 2005/0027304 A1 | 2/2005 | Leloup et al. | |
| 2005/0065617 A1 | 3/2005 | Moctezuma de la Barrera et al. | |
| 2005/0075632 A1* | 4/2005 | Russell ........................... | 606/53 |
| 2005/0288679 A1 | 12/2005 | Kienzle | |
| 2006/0064106 A1 | 3/2006 | Fernandez | |
| 2006/0084867 A1 | 4/2006 | Tremblay et al. | |
| 2006/0098851 A1 | 5/2006 | Shoham et al. | |
| 2006/0161059 A1 | 7/2006 | Wilson | |
| 2006/0173293 A1 | 8/2006 | Marquart et al. | |
| 2006/0241416 A1 | 10/2006 | Marquart et al. | |
| 2006/0281334 A1 | 12/2006 | Shin et al. | |
| 2007/0038059 A1 | 2/2007 | Sheffer et al. | |
| 2007/0038223 A1 | 2/2007 | Marquart et al. | |
| 2007/0161929 A1 | 7/2007 | Maier | |
| 2007/0270680 A1 | 11/2007 | Sheffer et al. | |
| 2008/0018643 A1* | 1/2008 | Feilkas et al. ................ | 345/420 |
| 2008/0051910 A1 | 2/2008 | Kammerzell et al. | |
| 2008/0075348 A1 | 3/2008 | Rappaport et al. | |
| 2008/0089566 A1 | 4/2008 | Node-Langlois et al. | |
| 2008/0119725 A1 | 5/2008 | Lloyd | |
| 2008/0243191 A1 | 10/2008 | Tipirneni et al. | |
| 2008/0269596 A1 | 10/2008 | Revie et al. | |
| 2008/0281334 A1 | 11/2008 | Zheng et al. | |
| 2008/0294265 A1 | 11/2008 | Warkentine et al. | |
| 2008/0319448 A1 | 12/2008 | Lavallee et al. | |
| 2009/0209851 A1 | 8/2009 | Blau | |
| 2009/0234217 A1 | 9/2009 | Mire et al. | |
| 2010/0030219 A1 | 2/2010 | Lerner et al. | |
| 2010/0104150 A1 | 4/2010 | Saint Felix et al. | |
| 2010/0168562 A1 | 7/2010 | Zhao et al. | |
| 2011/0019884 A1 | 1/2011 | Blau | |
| 2011/0184477 A1 | 7/2011 | Dell'Oca et al. | |
| 2011/0213379 A1 | 9/2011 | Blau et al. | |
| 2011/0313418 A1 | 12/2011 | Nikonovas | |
| 2013/0060146 A1 | 3/2013 | Yang et al. | |
| 2013/0211244 A1 | 8/2013 | Nathaniel | |
| 2013/0322726 A1 | 12/2013 | Nathaniel | |
| 2017/0128027 A1 | 5/2017 | Nathaniel et al. | |

FOREIGN PATENT DOCUMENTS

| | | |
|---|---|---|
| CN | 101069640 A | 11/2007 |
| DE | 102005062610 A1 | 6/2007 |
| DE | 102005062611 A1 | 6/2007 |
| DE | 102007008521 A1 | 8/2007 |
| DE | 102007008522 A1 | 8/2007 |
| EP | 0738502 A2 | 10/1996 |

(56) References Cited

FOREIGN PATENT DOCUMENTS

| | | |
|---|---|---|
| EP | 1491151 A1 | 12/2004 |
| EP | 1523950 A1 | 4/2005 |
| EP | 1859755 A2 | 11/2007 |
| EP | 1994914 A1 | 11/2008 |
| FR | 2895267 A1 | 6/2007 |
| GB | 2421187 A | 6/2006 |
| JP | 2008514296 A | 5/2008 |
| JP | 2010538753 A | 12/2010 |
| WO | WO 9804203 A2 * | 2/1998 |
| WO | 0209611 A2 | 2/2002 |
| WO | 03105659 A2 | 12/2003 |
| WO | 2004069040 A2 | 8/2004 |
| WO | 2005087125 A2 | 9/2005 |
| WO | 2007073733 A1 | 7/2007 |
| WO | 2007095917 A2 | 8/2007 |
| WO | 2007095918 A1 | 8/2007 |
| WO | 2007095919 | 8/2007 |
| WO | 2009087214 A1 | 7/2009 |
| WO | 2012007054 A1 | 1/2012 |
| WO | 2012084056 A1 | 6/2012 |

OTHER PUBLICATIONS

Communication from EP Application No. 10153136 dated Aug. 17, 2011.

Jagannathan et al., Neurosurg Focus 20, 2, E9, pp. 1-6, 2006.

International Search Report, PCT/EP2009/050210, dated Jun. 16, 2009.

Amir Herman et al., The International Journal of Medical Robotics and Computer Assisted Surgery, 5; 45-50, Dec. 29, 2008.

Thomas C. Kienzle III et al., "An Integrated CAD-Robotics System for Total Knee Replacement Surgery", IEEE, 1993.

Joskowicz et al., IEEE Transactions on Medical Imaging, IEEE Service Center, Piscataway NJ, US, vol. 24, No. 5, May 1, 2005, pp. 624-635.

PCT International Search Report PCT/EP2010/060314 dated Apr. 6, 2011.

Ziv Yaniv, Member, IEEE, and Leo Joskowicz, Senior Member, IEEE, Precise Robot-Assisted Guide Positioning for Distal Locking of Intramedullary Nails, IEEE Transactions on Medical Imaging, vol. 24, No. 5, May 2005.

Hofstetter et al., "Computer-Assisted Fluoroscopy-Based Reduction of Femoral Fractures and Antetorsion Correction", Computer Aided Surgery 5:311-325 (2000).

International Search Report for PCT/EP2012/004102 dated Feb. 27, 2013.

Schulz et al., "Evidence Based Development of a Novel Lateral Fibula Plate (VariAx Fibula) Using a Real CT Bone Data Based Optimization Process During Device Development", The Open Orthopaedics Journal, 6:1-7 (2012).

\* cited by examiner

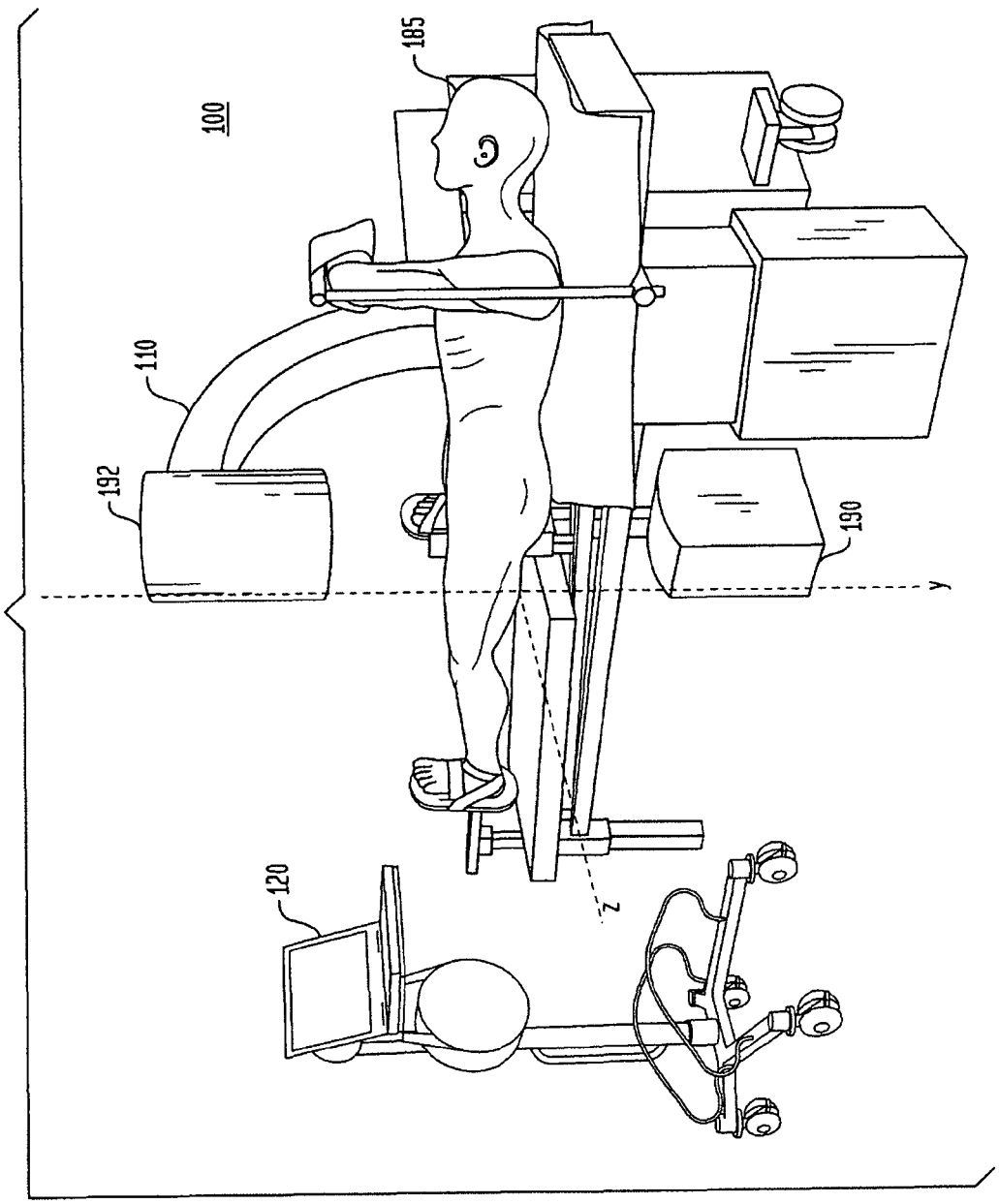

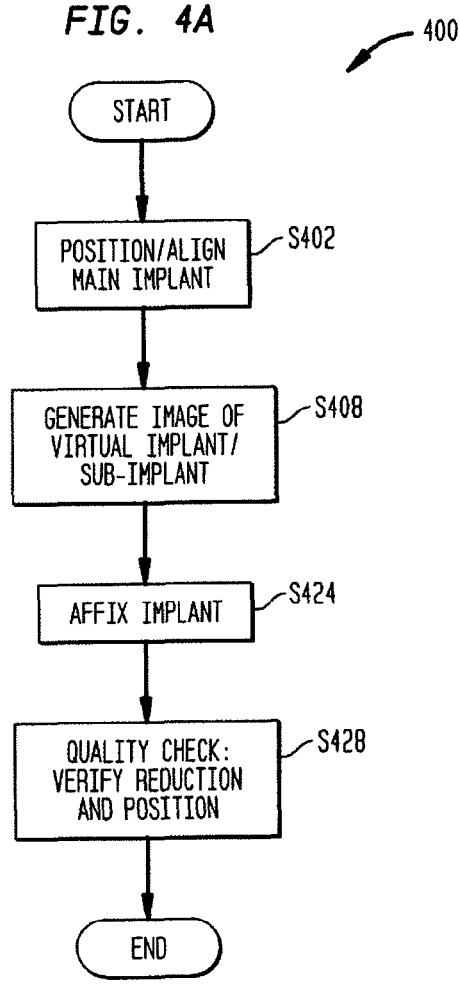

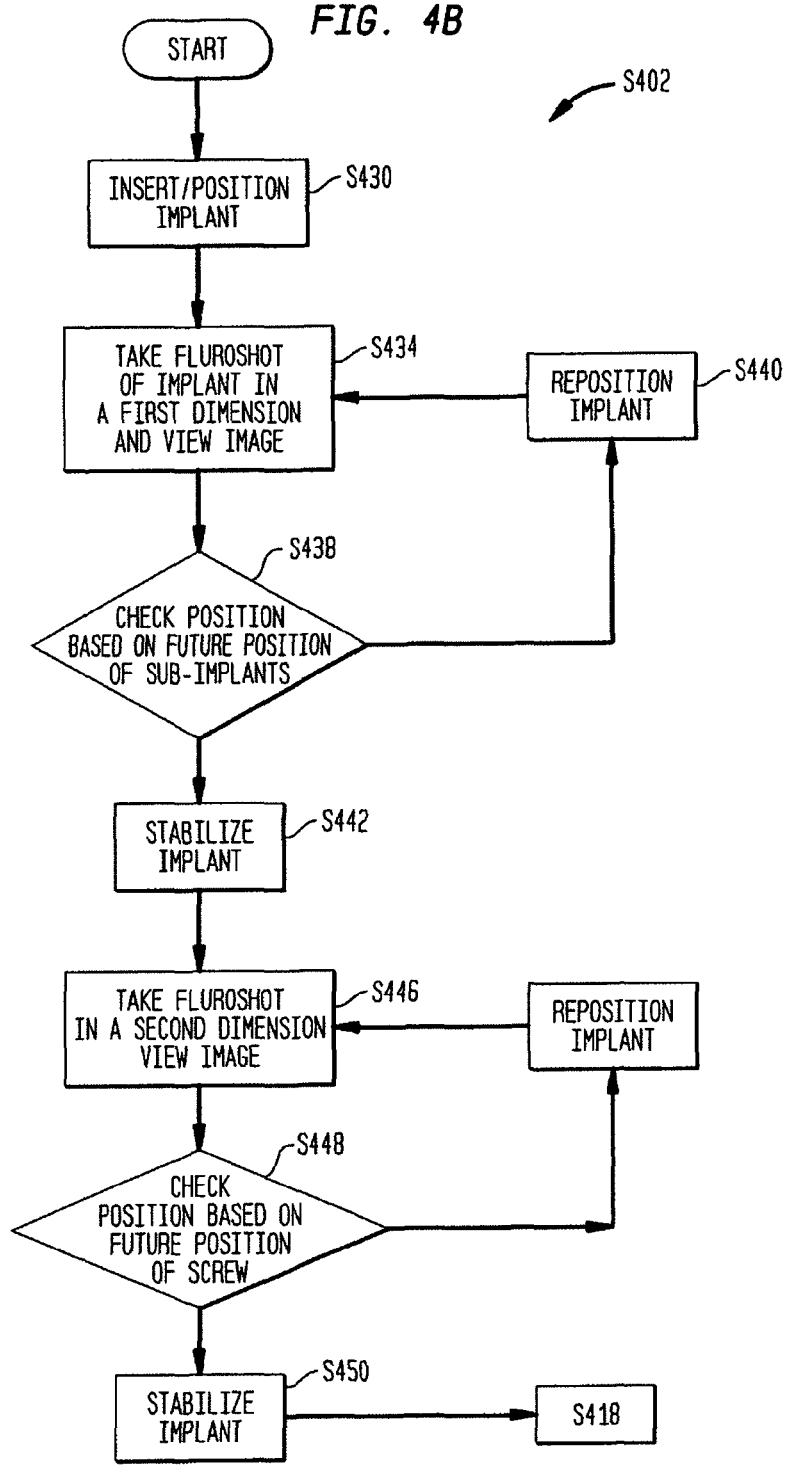

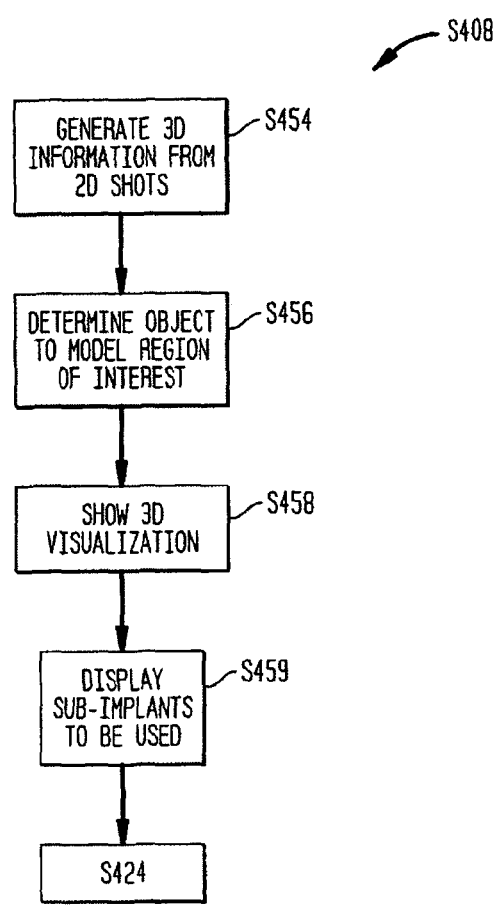

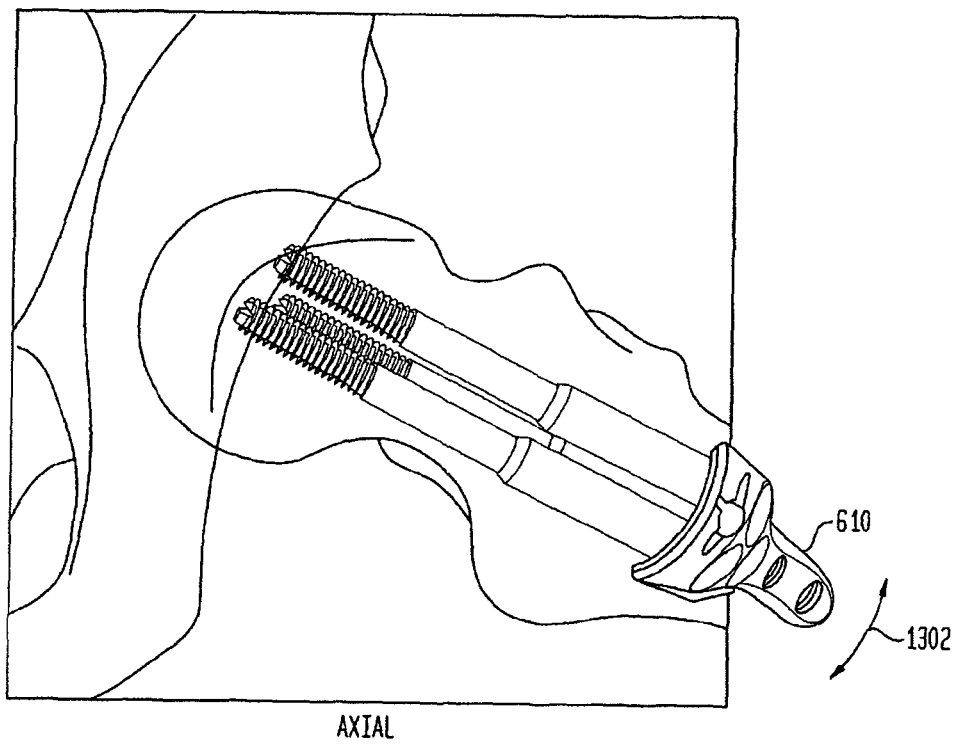

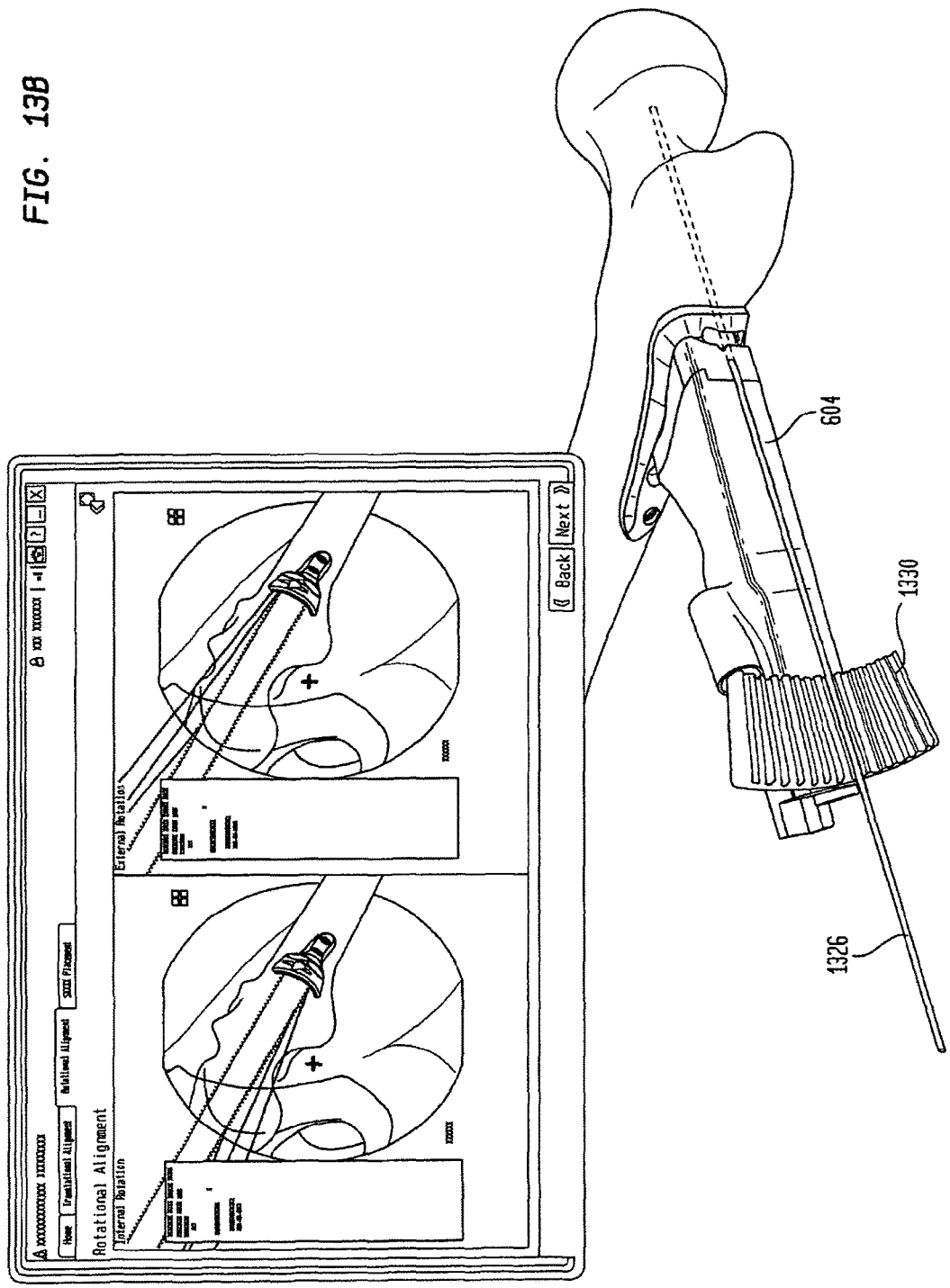

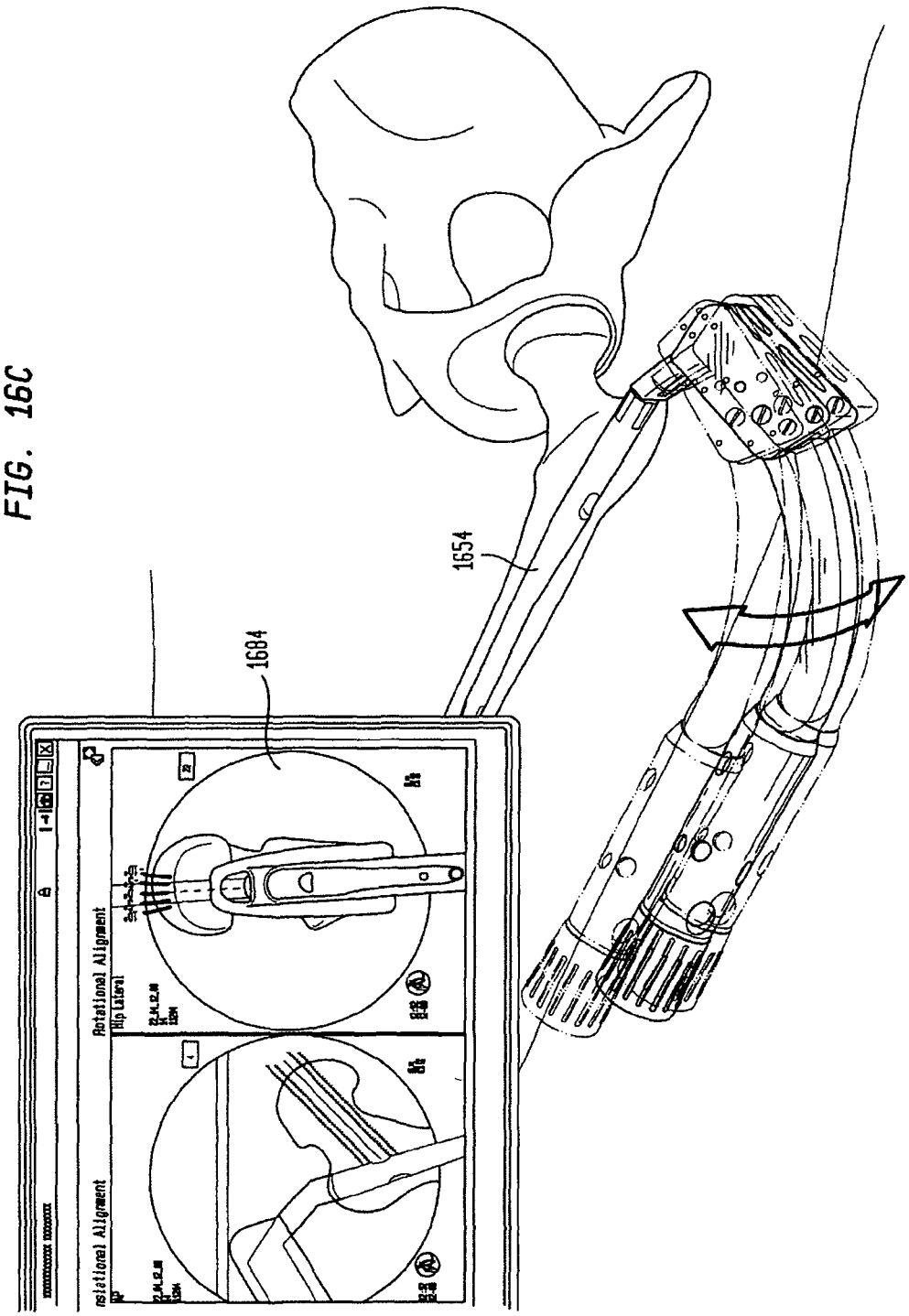

STEREOTACTIC COMPUTER ASSISTED SURGERY BASED ON THREE-DIMENSIONAL VISUALIZATION

CROSS-REFERENCE TO RELATED APPLICATIONS

The present application is a national phase entry under 35 U.S.C. § 371 of International Application No. PCT/EP2009/050210, filed Jan. 9, 2009, published in English, which claims the benefit of U.S. Provisional Patent Application No. 61/010,543, filed Jan. 9, 2008. The disclosures of said applications are incorporated by reference herein.

BACKGROUND OF THE INVENTION

The invention relates to a system and method of computer assisted surgery (CAS) using stereotactic navigation with three-dimensional visualization, and more specifically to a CAS system that is reactive and does not disrupt operating room workflow procedures.

A current method of inserting implants (consisting of, for example, a plate and associated screws) is typically accomplished by positioning the plate on the corresponding anatomical location and inserting the screws with the assistance of fluoroscopy. The implantation of plating and nailing systems is often a difficult task because operating room (OR) procedures are generally minimally invasive and thus placement is achieved by trial and error using fluoroscopy such as a C-arm apparatus, i.e., C-arm vision. This generally leads to long operating times. Furthermore, during such a procedure, both the patient and the operator are exposed to significant amounts of radiation.

In addition, in some cases it may be impossible to determine the position of implant components (for example, the screws in the bone) with sufficient precision because the fluoroscopic image is only two-dimensional. This may lead to misplacement or insertion of screws of improper length. This, in turn, may cause high revision rates or even injuries (e.g., hip joint injury). In order to ensure that these implant components do not extrude from the bone, it is thus sometimes necessary to position these implant components with an excessively large margin of error away from the edge of the bone. In many instances, the result is that the implant cannot be positioned as intended, and the desired biomechanical stability cannot be achieved. In the case of femoral neck fractures, for example, the use of conventional fluoro-navigation does not result in any significant improvement.

Other cutting edge technologies currently being used in operating rooms to assist in surgery include intra-operative three-dimensional (3D) imaging and navigation systems based on tracking technology. However, only a few hospitals are using these technologies. The limited adoption of these technologies is primarily due to their high cost, the effort involved in installing these systems, and the significant resulting changes to OR procedures or workflow. For example, tracking technologies require a line of sight between the tracking device and navigation detection system. This disrupts the normal workflow since the surgeon and other personnel must then remain cognizant of the system's line of sight requirements.

Further, as a general matter, satisfactory positioning of a main implant, like a plate or nail, cannot be defined pre-operatively. For example, during an operation positioning can be done by haptic match on the bone surface or by reaming the bone to make space for an intra-medullary nail. In addition, although the position of sub-implant(s) might be based only on pre-operative images (e.g., fluoroscope or CT images), such position is still relative to the position of the main implant. Thus, a positioning procedure cannot be completely planned pre-operatively, but must be optimized during the operation. In this regard, classical stereotaxis cannot be used due to the fact that the position cannot be predefined.

Accordingly, there is a need for a computer assisted surgery (CAS) system that enhances surgical procedures without significantly disrupting the normal OR workflow. More specifically, there is a need for a combined 3D imaging and CAS system which can be easily and readily integrated into the clinical environment. Preferably, such a system would be low cost, easy to set-up and use, and minimize changes to the OR workflow.

SUMMARY

An aspect of the present invention is a reactive method for stereotactic surgery. The method preferably comprises positioning an implant associated with a reference body on a region of interest of a patient's anatomy; detecting information associated with the implant using an imaging system; determining, based on the detected information associated with the implant, an action to be taken as part of the surgery; and displaying positional information associated with the implant and the region of interest based on the action to be taken.

In accordance with this aspect of the present invention, positioning comprises acquiring two fluoroscope images of the region of interest at two different angles.

Further in accordance with this aspect of the present invention, displaying further comprises processing detected information associated with the implant by estimating the contours of the region of interest in at least two dimensions based on the plurality of two-dimensional images.

Further still in accordance with this aspect of the present invention, detecting comprises detecting the presence of the reference body based on one or more fiducial markers.

In another aspect, the present invention is a method for stereotactic surgery. The method preferably comprises positioning a medical device associated with a reference body proximate a region of interest of a portion of an anatomy of a subject and imaging the region of interest at two or more angles to obtain a plurality of two-dimensional images. In a preferred embodiment, the reference body comprises a plurality of fiducial members, most preferably at least four such markers that are visible to the imaging system. It is further preferred that the fiducial markers comprise spheres that are visible to the imaging system.

In accordance with this aspect of the present invention, the plurality of two-dimensional images are processed to produce three dimensional information associated with the region of interest. In addition, the method further preferably includes associating, based on the three dimensional information, a virtual medical device with the region of interest and the reference body and displaying the association as an image showing the virtual medical device superimposed onto the region of interest.

Further in accordance with this aspect of the present invention, the virtual medical device comprises a main implant and one or more sub-implants. In addition, the virtual main implant is superimposed over the current location of the actual implant and the virtual sub-implants are generated so as to show its future position. Accordingly, the virtual sub-implants inform the surgeon of where the actual sub-implant will be located before it is placed in the region of interest.

In accordance with this aspect of the present invention, imaging preferably comprises acquiring two fluoroscope images of the region of interest at two different angles. In addition, processing further preferably comprises estimating the contours of the region of interest in at least two dimensions based on the plurality of two-dimensional images.

Further in accordance with this aspect of the present invention, processing may further comprise forming a three dimensional image associated with the region of interest based on the estimation. In a further preferred aspect, the present invention may be applied to a surgical implant procedure wherein the region of interest comprises a femoral head, the plurality of two dimensional images comprise anterior-to-posterior and axial images of the femoral region and estimating comprises forming an outline of the femoral head on the anterior-to-posterior and axial images. In this regard, the method may further comprise forming parts of a three dimensional sphere representing important portions of the femoral head.

Further still in accordance with this aspect of the present invention, the medical device preferably comprises an intracapsular plate and the reference body is connected to the plate, and positioning comprises positioning the intracapsular plate on a femur proximate the femoral head. In addition, the virtual medical device preferably comprises a virtual intracapsular plate and displaying comprises showing the virtual intracapsular plate superimposed on the position of the intracapsular plate in relation to the femoral head.

In another aspect, the present invention is a computer assisted surgical system, comprising: an apparatus for imaging a region of interest of a portion of an anatomy of a subject; a memory containing executable instructions; and a processor programmed using the instructions to perform a method. In this regard, the processor preferably receives two or more two-dimensional images of the region of interest taken at different angles from the apparatus, processes the two or more two-dimensional images to produce three dimensional information associated with the region of interest, superimpose a virtual reference body onto the region of interest based on the three dimensional information to form an image showing the virtual reference body relative to the region of interest, and generate a display signal associated with the superimposed image. Preferably, the reference body is first detected and superimposed onto an object that models the region of interest, e.g., sphere for a femoral head; and the display signal is then generated.

In accordance with this aspect of the present invention, the processor preferably processes the one or more two-dimensional images by outlining the contours of the region of interest in two dimensions and creates a three dimensional object representing the region of interest. The three dimensional object may be derived from a database and based on age and gender of the patient. The three dimensional object may also be determined based on landmarks associated with the region of interest.

Further in accordance with this aspect of the present invention, a medical device may comprise a device selected from the group consisting of an intracapsular plate, an artificial joint, a pacemaker and a valve.

In another aspect, the present invention is a system and method of computer assisted surgery (CAS) using stereotactic navigation with three-dimensional visualization, wherein an implant or implant system acts as a stereotactic device. The invention provides a reactive CAS system designed for use with mono-axial and poly-axial plates and nails. Based on the principles of stereotactics and 2D-3D matching, a system is provided that virtually suggests or gives indication of the optimal position of an implant by calculating such position. In addition, the system may also calculate screw lengths before drilling. Aided by image processing and virtual 3D visualisation, the system can achieve optimal biomechanics.

In addition, unlike existing navigation systems, the CAS system of the present invention is designed to be reactive to reduce any additional effort for the surgeon. In particular, the system may be triggered by use of a reference body, implant K-wires, or screws that are normally used as part of the surgical procedure. In addition, by detecting these devices, the system is able to determine the step in the workflow that's being performed. More specifically, image processing is used to detect various objects during the workflow and determine which step is being performed by the surgeon and for system adaptation.

In another aspect, the system provides necessary 3D information without the need for intra-operative 3D imaging (e.g. 3D C-arms). The system is also low cost, easy to set-up and use, and minimizes changes to the OR workflow. The present system also requires fewer X-ray images and is therefore safer for patients.

In another aspect, the invention makes use of an iterative procedure (which for the example of using an ICP to fix a femur neck fracture) includes one or more of the following steps:

1. positioning an implant in an anatomical region of interest, e.g., based on a satisfying haptic match;
2. fluoroscopic imaging of the anatomical region of interest;
3. virtually checking the future position of the sub-implant(s);
4. virtually realigning the implant according to constraints until a satisfactory virtual position is reached;
5. providing active or passive realignment values for position of the implant to the surgeon (i.e., actively by identifying the best location or passively by allowing the surgeon to decide;
6. actual realignment of the plate by the surgeon based on realignment values and a satisfactory haptic match; and
7. iterate procedure starting at step 2 until operation complete.

These and additional aspects and features of the present invention are described in further detail below.

BRIEF DESCRIPTION OF THE DRAWINGS

FIG. 1A illustrates a stereotactic computer assisted surgical system in accordance with an aspect of the present invention.

FIG. 4A is a flowchart illustrating a procedure for implanting a medical device in accordance with an aspect of the present invention.

FIG. 4B is a flowchart illustrating a procedure for positioning an implant in accordance with an aspect of the present invention.

FIG. 4C is a flowchart illustrating a procedure for generating a virtual image of an implant and a region of interest.

FIG. 13A shows a step of automatically adjusting the proposed position of the intracapsular plate by external rotation.

FIG. 13B shows a step of automatically adjusting the proposed position of the intracapsular plate by external rotation.

FIGS. 16A-16H illustrate use of the method of FIG. 4 in accordance with an aspect of the present invention.

DETAILED DESCRIPTION

Generally, in one aspect, the system of the present invention is based on the registration of fluoroscopy images with an implant associated with a reference body. For example, the implant (e.g., an angle stable plate) may include the reference body or may be positioned in a predefined location in relation to the reference body, which is detected or recorded in a fluoro image. Thus, the actual spatial dimension and position of the implant can be determined by means of the correct identification and registration of the reference body in the fluoro images.

Where multiple related implants are included as part of the procedure, e.g., main implants and sub-implants, after registration of the main implant as described above, the location of any remaining sub-implants may be depicted virtually in the correct spatial position in relation to the fluoro images of the main implant. The sub-implants (e.g., screws of the associated angle stable plate) will be located in a fixed, pre-defined position in relation to the main implant after all implants have been implanted.

In order to provide the information necessary for an anatomically correct location of all (main and sub-) implants, important anatomical regions are approximated using three dimensional bodies or objects depicted in the fluoro image in correct relative position. Target values are compared with the values of the location of the remaining implants, which are used in determining the current position of the main implant.

During pre-operative planning (for example, using a non-invasive applied reference body), the partial or sub-implants (e.g., screws) can first be placed in an optimum position, independent of the location of the main implant (plate). In a subsequent operation (using an invasive reference body), where the main implant location has been determined by the pre-operative planning (with a position estimate derived by the surgeon), the location of the main implant can be optimized using haptic feedback. After the registration as described above, the resulting location of the partial or sub-implants are depicted virtually; this position is compared to the position of the partial implant in the pre-operative plan, and to the distances to important anatomical (three-dimensional) structures. In a reactive iterative process (adjusting the plate as instructed by the system), it is possible to determine the optimum balance between an ideal main implant location (for example, plate fit) and the ideal partial implant position (for example, screw location).

Figure 1B:
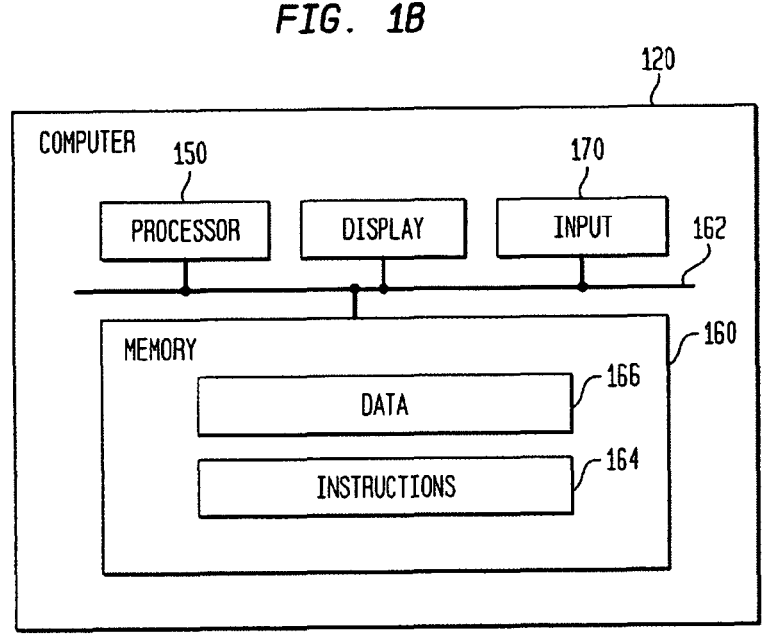
FIG. 1B depicts a computer that may be used in the system of FIG. 1 in accordance with an aspect of the present invention.

Turning now to FIG. 1A, there is illustrated a stereotactic computer assisted surgical (CAS) system 100 in accordance with an aspect of the present invention. As shown, in the preferred embodiment, the system 100 includes an imaging apparatus 110, such as a C-arm fluoroscope, and a computer device 120 such as laptop computer. In general, the computer device 120 contains a processor 150, memory 160 and other components typically present in general purpose computers as depicted in FIG. 1B.

Memory 160 stores information accessible by processor 150, via bus 162 for example, including instructions 164 for execution by the processor 150 and data 166 which is retrieved, manipulated or stored by the processor 150. The memory 160 may be of any type capable of storing information accessible by the processor 150, such as a hard-drive, ROM, RAM, CD-ROM, write-capable, read-only, or the like. The instructions 164 may comprise any set of instructions to be executed directly (such as machine code) or indirectly (such as scripts) by the processor. In that regard, the terms "instructions," "steps" and "programs" may be used interchangeably herein. The functions, methods and routines of the program in accordance with the present invention are explained in more detail below.

Data 166 may be retrieved, stored or modified by processor 150 in accordance with the instructions 164. The data may be stored as a collection of data. For instance, although the invention is not limited by any particular data structure, the data may be stored in computer registers, in a relational database as a table having a plurality of different fields and records, or as an XML document. The data may also be formatted in any computer readable format such as, but not limited to, binary values, ASCII or EBCDIC (Extended Binary-Coded Decimal Interchange Code). Moreover, any information sufficient to identify the relevant data may be stored along with the data, such as descriptive text, proprietary codes, pointers, or information which is used by a function to calculate the relevant data.

Although the processor 150 and memory 160 are functionally illustrated in FIG. 1B within the same block, it will be understood by those of ordinary skill in the art that the processor 150 and memory 160 may actually comprise multiple processors and memories that may or may not be stored within the same physical housing. For example, some or all of the instructions 164 and data 166 may be stored on removable CD-ROM and others within a read-only computer chip. In addition, some or all of the instructions 164 and data 166 may be stored in a location physically remote from, yet still accessible by, the processor 150. Similarly, the processor 150 may actually comprise a collection of processors which may or may not operate in parallel.

As shown, computer device 120 may comprise additional components typically found in a computer system such as a display (e.g., an LCD screen), user input (e.g., a keyboard, mouse, game pad, touch-sensitive screen), microphone, modem (e.g., telephone or cable modem), and all of the components used for connecting these elements to one another.

As is also shown in FIG. 1A, a patient 185 would typically be positioned on an operating table with various restraints such that the area to be operated on is constrained from moving during the surgery. The fluoroscope 110 (or other suitable imaging apparatus) is used to obtain images of the region of interest of the patient's anatomy, e.g., the region being operated on or area to which the implant will be attached. As is discussed in further detail below, an illustrative region of interest may comprise an area that includes the femoral neck and an intracapsular plate (ICP). The computer 120 (or other suitable image processing and display apparatus) is used to process the images from the fluoroscope, determine positioning for the implant and sub-implants, and provide feedback/instructions to the surgeon. The processing steps performed by the computer are described below.

In another aspect, the present invention addresses a problem with the current technique of ICP implantation of accurately positioning the plate using two-dimensional (2D) images. This problem is in part due to the dangerous screw placement needed to avoid cutouts. Specifically, the ends/tips of the screws need to be set as close as possible to the second cortex. However, the 2D images used by the surgeon do not reflect the 3D nature of the problem.

Figure 2:
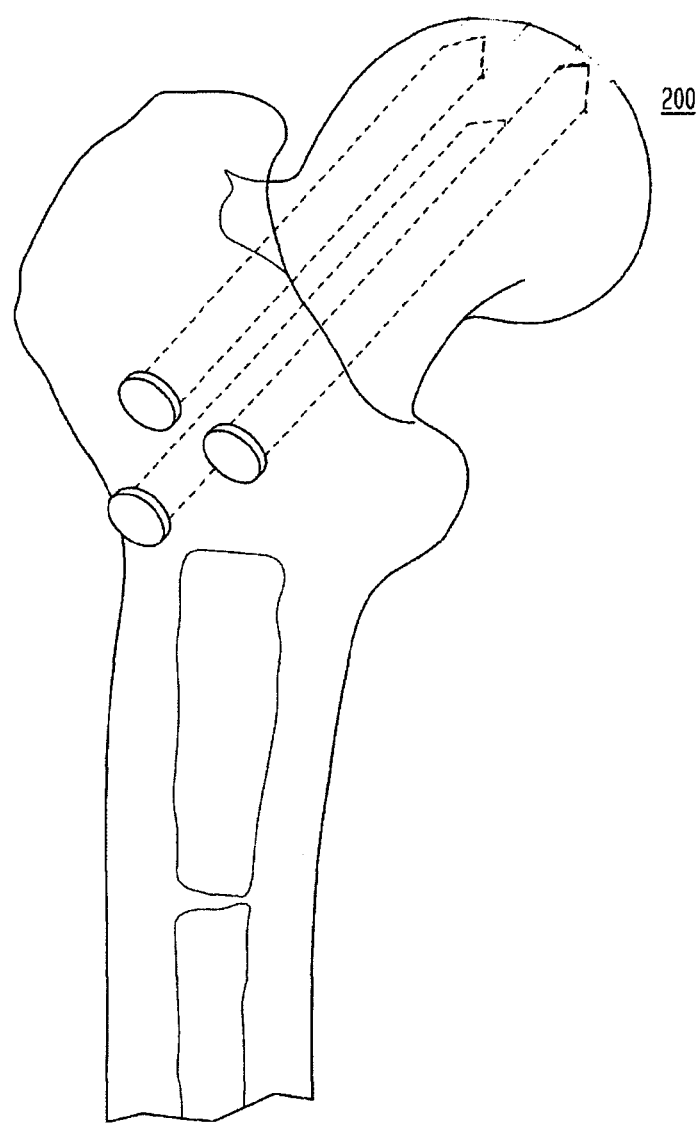
FIG. 2 illustratively depicts how a conventional two-dimensional (2D) image may not accurately show the positions of screws in a region of interest.
Figure 3:
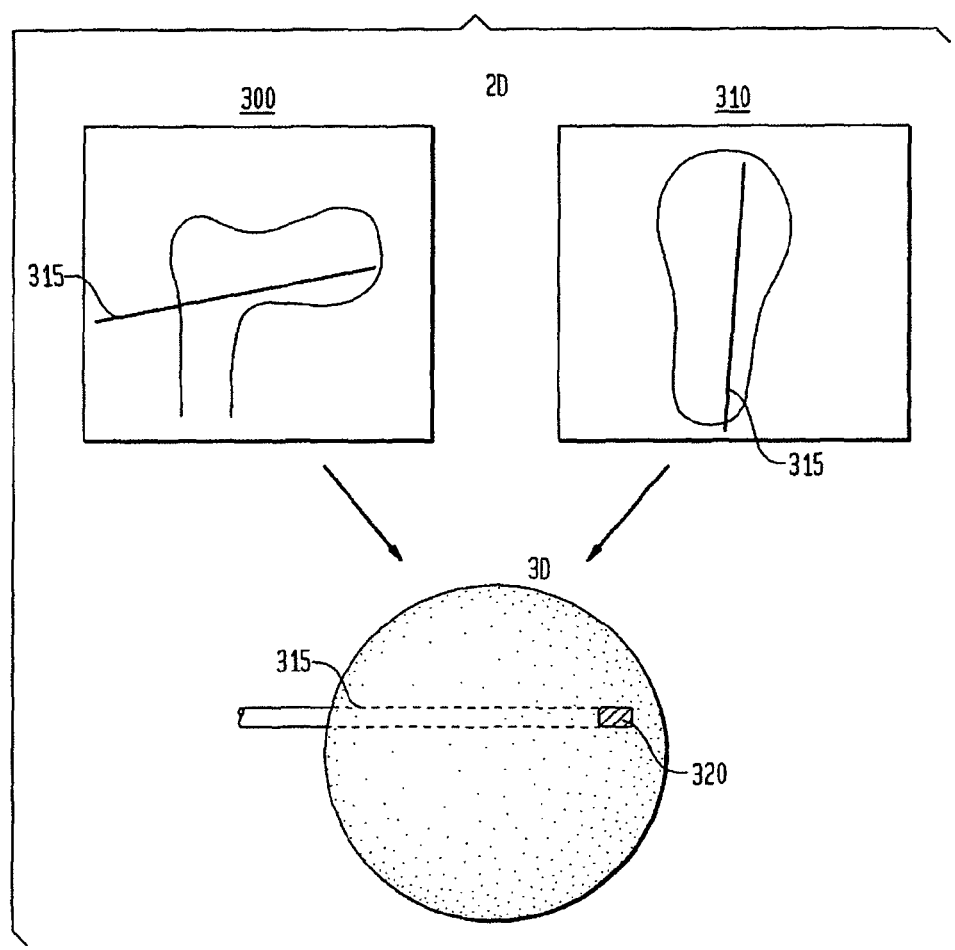
FIG. 3 illustratively depicts how three-dimensional imagery may be used to depict the positional information that is not apparent with conventional two dimensional images.

FIG. 2 shows common drawbacks of a conventional two-dimensional (2D) image. In particular, a 2D image 200 may not indicate improper positioning of a screw. In this instance, the 2D image 200 makes it appear that the screws are correctly positioned within the bone. However, a 3D illustration could provide additional information showing that a screw may actually have perforated the bone. For example, FIG. 3 illustrates how 3D imagery may expose a problem with screw positioning that is not apparent with conventional 2D imaging. In FIG. 3, neither of the 2D images 300, 310 shows a problem with the screw position. However, if the 2D images are combined to create a 3D visualization, it becomes apparent the tip of the screw projects through the bone as illustrated at 320. Hence, the 2D imagery currently relied upon by a surgeon may not always accurately reflect the location and positioning of medical devices and the like within a region of interest. Thus, in this example, it would be beneficial for a surgeon to have access to 3D imagery.

In one aspect, the present invention provides a system and method which generates 3D information from the 2D imagery to allow for more accurate positioning of a medical device, e.g., an implant, and thereby avoiding the above problems. Generally, as used herein, the term medical device includes any biomedical device or structure that is introduced or implanted into the anatomy of a subject. Such devices include those that replace or act as missing biological structures, or that are placed over or within bones or portions of the anatomy. As mentioned above, the present invention is described using the illustrative example of implanting an intracapsular plate (ICP) to repair a femoral neck fracture. Note, however, that the invention may find application in numerous surgeries, including virtually all fields of bone surgery (e.g., trauma, orthopedics, and pediatrics).

By way of background, it is generally known that fractures are usually repaired by reduction and fixation of the broken bones. The individual fragments of bone are aligned in their normal anatomical position (i.e., reduced) so that separated parts can grow together again. It is necessary that the parts remain relatively stable with respect to each other over an extended period of time to allow for healing. In some cases, particularly for more complicated fractures, it is necessary to connect the individual broken bone pieces directly to one another. In these cases, the fracture is fixed or reduced via an invasive procedure wherein an implant is installed within the body with screws or nails.

Turning now to FIG. 4A, there is depicted a high level flowchart 400 of the method steps of implanting an implant in accordance with an aspect of the present invention. As shown, the method begins with positioning of a main implant in a region of interest, at step S402. As is explained in further detail below, this initial positioning is preferably done using fluoroshots taken along at least two dimensions or directions. Once the main implant is positioned to the surgeon's satisfaction, the system 100 generates an image showing the position of a virtual implant and associated virtual sub-implants relative to the region of interest, step S408, based on the fluoroshots and the position of a reference body or reference objects within the field of view of the fluoroscope 110.

Using the image of the virtual implants, the surgeon may then affix the implant, using the sub-implants for example, as is depicted at S424. Once the sub-implants (e.g., screws) and implants are in the place, the system may perform a quality check, at S428, by detecting and displaying the actual location of these implants relative to their desired position. This quality check is desirable given that during implantation, the position of an implant or sub-implant may change from its ideal position due to the mechanical forces during, for example, drilling or screw placement or as a result of movement by the patient. In this regard, quality checks, such as step at S428, may also be performed during affixation of implant, at step S424. Additionally, quality checks may also be performed post operatively using the system to detect movement in the implant caused by, for example, patient activity.

Significantly, the above method 400 is reactive in that the surgeon is not required to inform the system 100 of which step he/she is performing as part of the OR workflow. In this regard, this system 100 is compatible with the normal OR workflow and is able to determine the step in the OR workflow that is being performed by, for example, detecting the presence of a reference body or object.

Turning now to FIG. 4B, there is depicted the sub-steps or procedure for positioning or aligning the implant in accordance with step S402 of FIG. 4A. As shown, the procedure begins with insertion and positioning the main implant in the anatomical region of interest at step S430. In keeping with the illustrative example, an intracapsular plate (ICP) is used to repair fractures of the femoral neck. Thus, at step S430, the ICP would be inserted into the patient and roughly positioned on the bone, in this case the femoral neck. This step may be done, for example, in accordance with the normal OR workflow, such as by allowing the doctor to use haptic feedback to judge an appropriate initial position for the plate.

Figure 5:
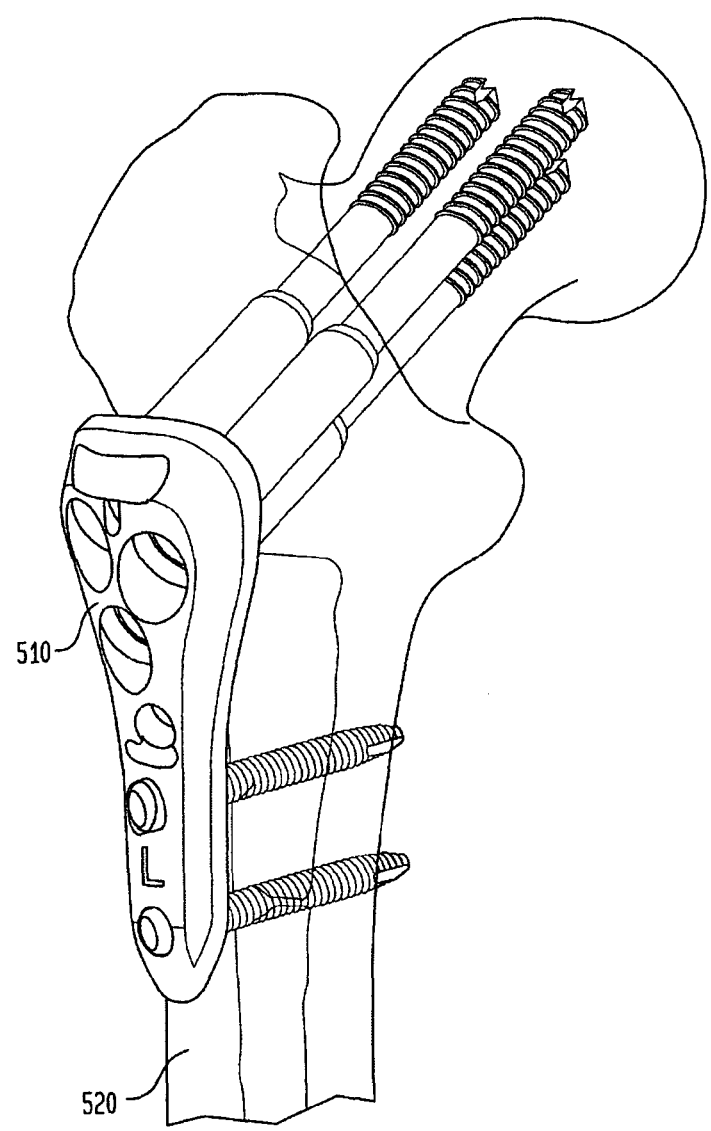
FIG. 5 shows the placement of an intracapsular plate implant in accordance with an aspect of the present invention.

In this regard, FIG. 5 illustrates the placement of an ICP implant 510 (e.g., the main implant) along with sub-implants (i.e., the screws) to secure a femoral neck fracture. As shown, the ICP 510 is affixed to the femur 520 and screws are inserted through the neck and head of the ICP. Preferably, in accordance with an aspect of the present invention, the screws entering the femoral head are positioned entirely within the head. In an additional aspect of the present invention, as the ICP is contoured to the shape of the femur, the degrees of freedom in positioning the ICP on the bone are limited and are used as part of the alignment procedure S402. Specifically, the ICP can only be shifted along (i.e., translation) and/or rotated around the shaft axis of the femur. In addition, the ICP has threaded holes so that the position/angle of the screws relative to the plate is known.

In accordance with an aspect of the present invention, prior to insertion of the main implant within the region of interest, the main implant 510 is connected to a reference body or object. The reference body is preferably attached to (or part of) the implant, but may also be attached to an aiming device or instrument (e.g., a drill guide). In this way, the position of the implant may be determined based on the location and position of the reference body. Preferably, each implant is associated with a different reference body that is detectable by the system 100, in particular the fluoroscope 110. In a preferred embodiment, the reference body comprises a plurality of spherical fiducial markers inserted on or in the instrument (e.g., aiming device). By arranging the fiducial markers in a predetermined pattern, they may serve as identifiers for different instruments. In this regard, the fiducial markers and instrument may be conveniently referred to as a reference body—though the fiducial markers are what provide the reference.

Figure 6A:
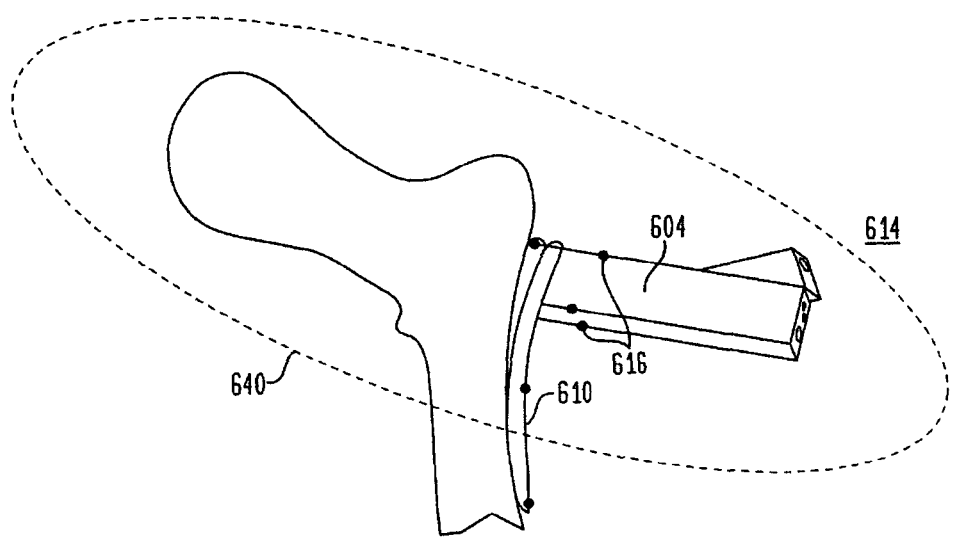
FIG. 6A is a side view of an implant system including a reference body and an implant in accordance with an aspect of the present invention.

For example, FIG. 6A illustrates a side view of a reference body 604 as part of the implant 610. Together, the reference body and implant are referred to herein as an implant system 614. As shown in FIG. 6A, the reference body 604 includes a one or more fiducial markers 616 that are detected by the imaging system and used as points of reference or measurement. Preferably, the fiducial markers comprise spheres to make for easier detection in a two-dimensional imaging system such as a fluoroscope. In addition, the arrangement of the fiducial markers within the reference body functions as signature that is used to identify the reference body and the associated implant. Given that the dimensions of the reference body and implant are known and these devices are fixed relative to each other, the location of the implant can be accurately determined by detecting or recording the location of the reference body. As is also shown in FIG. 6A, fiducial markers may also be placed on the implant itself, but are not necessary.

Figure 6B:
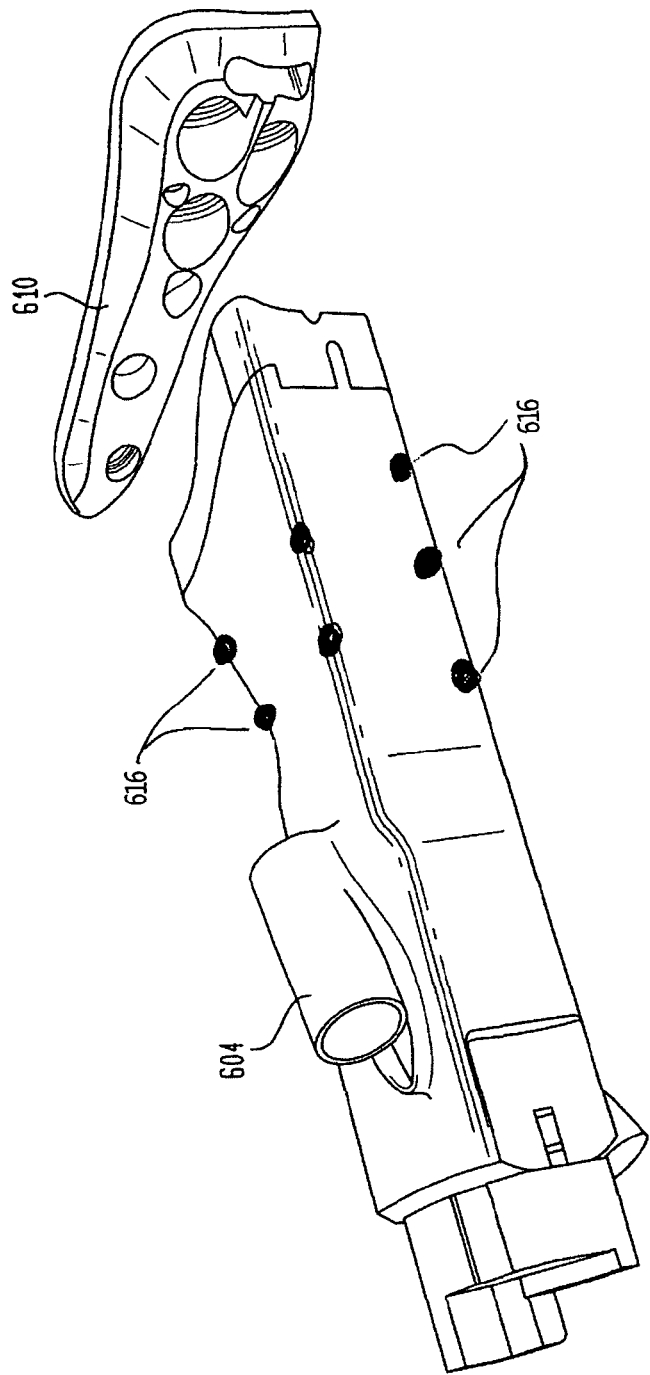
FIG. 6B is perspective view of a reference body and an implant in accordance with an aspect of the present invention.
Figure 6C:
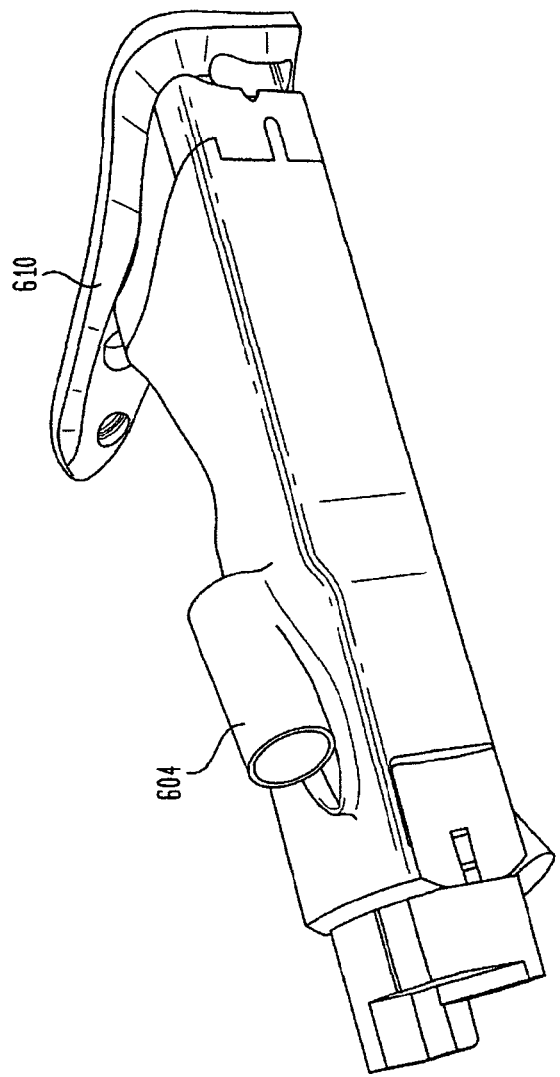
FIG. 6C is perspective view of a reference body and an implant in accordance with an aspect of the present invention.

FIG. 6B is a perspective view of the aiming device 604 and implant 610 (which in keeping with the example is an ICP) in a detached condition. FIG. 6C shows these two devices in an attached condition. As is shown, the aiming device 604 is contoured to fit the ICP 610. In addition, it includes openings that allow access to the screw holes on the ICP 610 that are used to secure the implant 610 as is explained in further detail below. To allow for processing, the reference body must be in the field of view of the image with the implant and the region of interest 640, which in keeping with this illustrative example includes the femur neck and femoral head. As part of this initial insertion and placement, the surgeon will typically use haptic feedback to determine a starting location for the implant.

Figure 7:
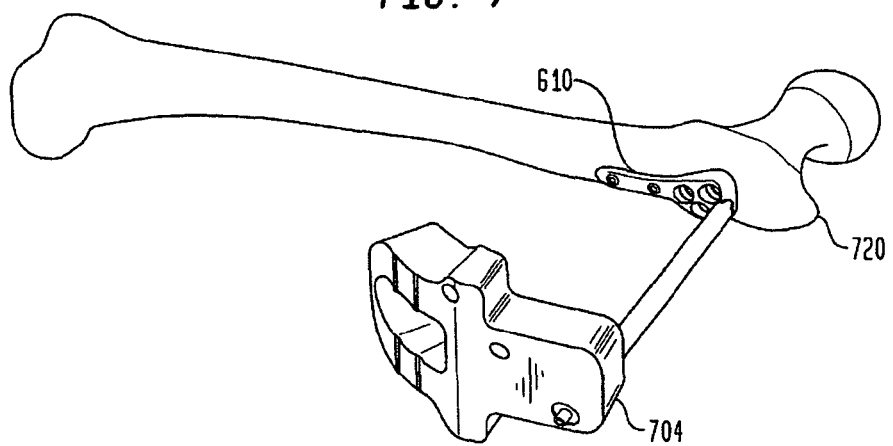
FIG. 7 illustrates the placement of an intracapsular plate implant onto a femur.

FIG. 7 shows an instrument 700 that may be used in the insertion and initial placement of the ICP 610 onto a femur 720. In addition, in making this initial placement, the surgeon may use either instrument 700 or reference body 604. In this regard, the instrument 700 may also comprise a reference body by placing the appropriate fiducial markers on or in it.

Figure 8:
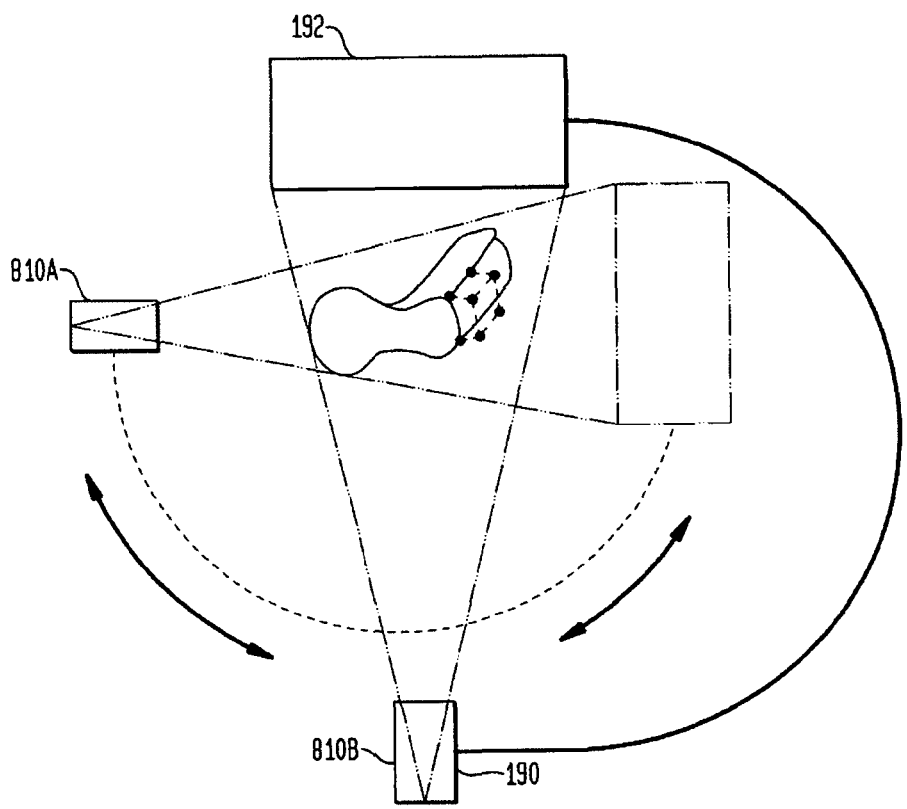
FIG. 8 illustratively depicts the step of taking two fluoroshots from different angles.

Returning to FIG. 4B, once the surgeon determines an initial location for the implant (and accompanying reference body), a fluoroshot is taken of a region of interest along a first dimension or direction, at step 434. For example, a fluoroshot may be taken along the anterior-posterior dimension or the axial dimension. With reference to FIG. 1, the anterior-posterior view is illustrated with the source 190 and detector 192 aligned along the y-axis, while in the axial view the source and detector are aligned along the z-axis As shown in FIG. 8, fluoroshots may be taken from any two different dimensions or directions 810A, 810B. Preferably, the two images will be taken perpendicular to one another (i.e. close to a 90 degree angle between them), but this is not required and any angle will suffice.

As the implant and reference body are located within the field of view of the imaging device, given their proximity to region of the interest, the fluoroscope 110 detects the presence of the reference body, i.e., the fiducial markers. Computer 120 then uses the image data it receives from the fluoroscope 110 to provide a visualization of the location of the implant relative to the region of interest. In particular, registration of the fluoroscopic images is performed using the reference body. As discussed above, the reference body is typically in a fixed position relative to the implant and bone. In addition, a disk is used at the image intensifier to develop the X-ray image. The disk is usually directly attached to the image intensifier. Such a reference body would also be seen in every image and could be used to compensate for distortion of the image and for determination of the center of, for example, the X-ray beam.

Determination of the implant relative to anatomical region of interest is done using known image processing techniques based on the variation in the spatial radiation arriving at the detector, including the radiation directed at the region of interest and reference body. Using the spatial variation, the computer is able to construction an image that accurately depicts the spatial relationship between the implant and region of interest (e.g., femur and femoral head) as a two dimensional image.

Upon viewing this image, the surgeon may then determine if the implant should be re-positioned, as at step S438. For example, the surgeon may decide to adjust the position along the length of the femur closer to the femoral head or other degree of freedom. If the surgeon decides such an adjustment is warranted, he/she repositions the implant as is shown at step S440 and additional fluoroshots are taken at step S434. On the other hand, if the surgeon determines that the no adjustment is needed along in this dimension the procedure continues at step S442 with stabilization of the implant. In keeping with the example, stabilization could be effected by insertion of a Kirshner wire (K-wire) through one or more openings in the ICP.

With the implant fixed as described above, a fluoroshot may then be taken along a different dimension, step S446. In particular, if the fluoroshots in step S434 were taken along the anterior posterior direction, in step S446 they may be taken along the axial direction or at another angle. In this regard, as part of step S402, it may be sufficient to use a single image for this step to optimize position along only one degree of freedom (e.g., a distal shift of the implant) where 3D information is not needed.

Upon completion of the fluoroshot at step S446, the surgeon may then view an image of the position of the implant. If it is determined that the implant needs to be adjusted at step S448, e.g., rotated in the case of an ICP, the procedure returns to step S446 and additional fluoroshots are taken along this dimension. Once the surgeon is satisfied that the implant is appropriately positioned based on images obtain along this dimension, the procedure continues at step S450 with additional stabilization of the implant. For example, where the implant or medical device is an ICP, K-wires may be inserted through additional openings in the ICP. As result of the foregoing procedure, the position of the ICP or other implant may be positioned by the surgeon iteratively and in accordance with normal OR workflow procedures. That is, the surgeon may repeat any steps within the procedure until the implant is appropriately positioned.

With the implant positioned as described above in relation to step S402, the method then continues as shown at step S408 of FIG. 4A and as will be now described in further detail as shown in FIG. 4C. In particular, at step S454, the system may then generate 3D information from the two dimensional fluoroshots recorded in step S402 or additional two dimensional fluoroshots may be taken at different angles as described above. Since the implant is now stabilized relative to the region of interest, additional fluoroshots may be taken with the K-wires acting as a trigger for the system. In addition, as the reference body may also be attached to the implant, it may also serve as a reference object as described above.

Figure 9:
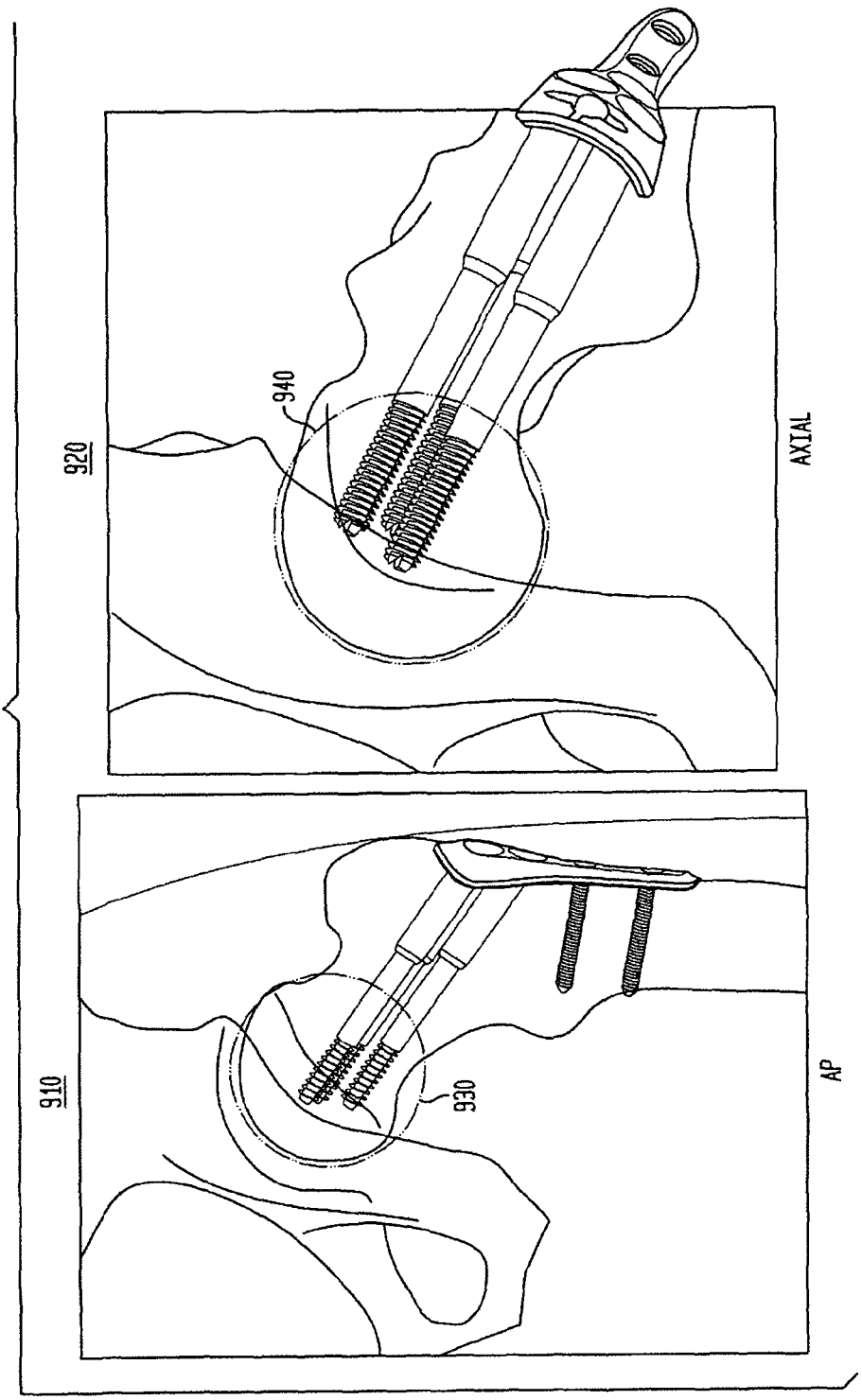
FIG. 9 illustrates detection of the femur head in the two fluoroshots.

In accordance with this aspect of the present invention, the resulting 2D images are processed to locate and outline a three dimensional contour, i.e., a sphere, of the femoral head. For example, FIG. 9 shows an AP view image 910 and an axial view image 920 with superimposed circles 930, 940 outlining the contours of the femoral head. The circles 930, 940 may be constructed by computer 120 using image processing techniques such as edge detection or computer generated models. Such models may be created pre-operatively using MRI or other non-invasive techniques that can determine the location and size of organs or bones within the region of interest.

Figure 10:
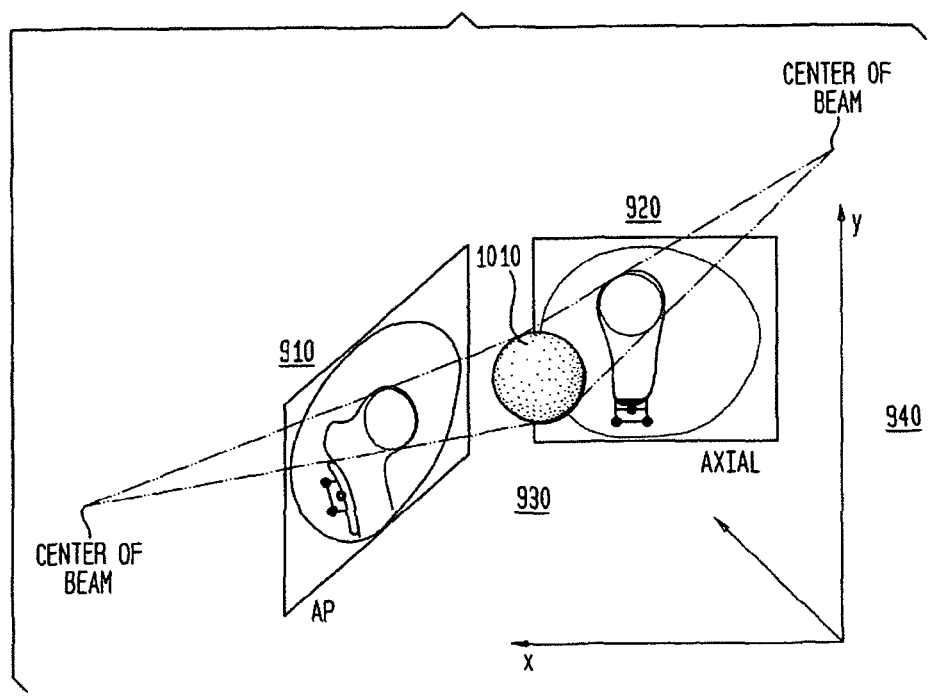
FIG. 10 illustrates the visualization of a virtual three dimensional sphere representing the femur head based on conical projections of the two dimensional fluoroshots.

In addition, using the 2D images, the computer 120 then determines and generates 3D object that is associated with and models the region of interest, step S456, in accordance with another aspect of the present invention. In particular, FIG. 10 illustrates the visualization of a virtual 3D sphere representing the femur head based on conical projections of the 2D images 910, 920. As shown in FIG. 10, the virtual 3D sphere is formed by projecting the two dimensional coordinate system onto a three dimensional coordinate system. In this example, as the outline of the femoral head forms circle, the projection onto a three-dimensional coordinate system results in a sphere. Depending on the contours of the region of interest, these projections may be done using a Cartesian and/or spherical coordinate system. In addition, the location of the object in relation to region of interest may be accurately determined based on the position of the implant in relation to the reference body.

Figure 11:
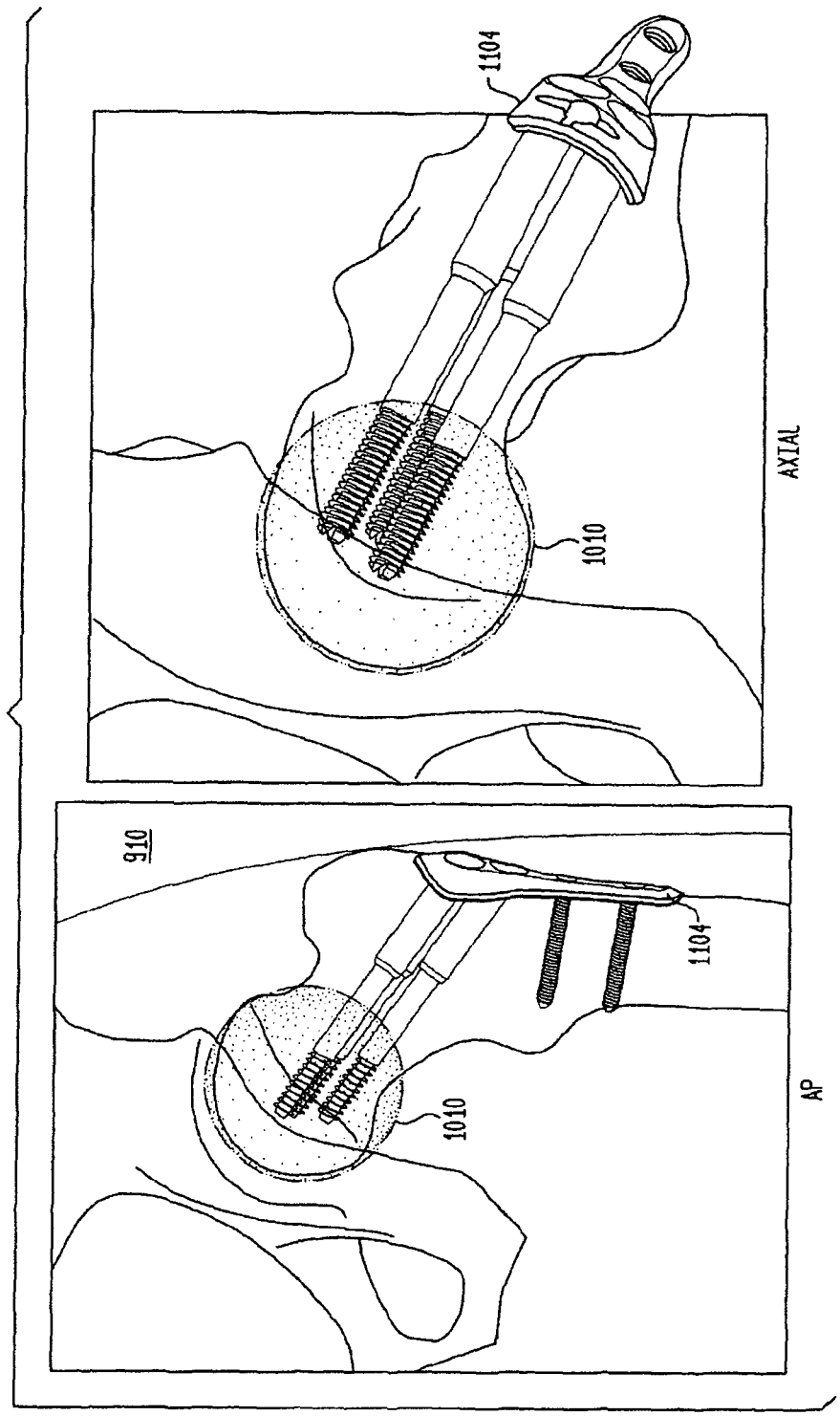
FIG. 11 shows the step of displaying a visualization based on a matching of the three dimensional sphere with the two dimensional images.

FIG. 11 shows the step of displaying a visualization of the region of interest, implants and sub-implants based on a matching of the 3D sphere with the 2D images, step S458.

As shown in FIG. 11A, the invention superimposes a virtual ICP 1104 with screws and a spherical outline of the femoral head onto the original 2D axial and AP images. This visualization allows the surgeon to readily see the position of the ICP and screws relative to the femoral head. Notably, the visualization shows the positions of virtual screws, their length and how they will be positioned within the femoral head. In addition, the system can suggest the screw, e.g., particular model, or screw length that would be suitable for affixing the implant.

Figure 12A:
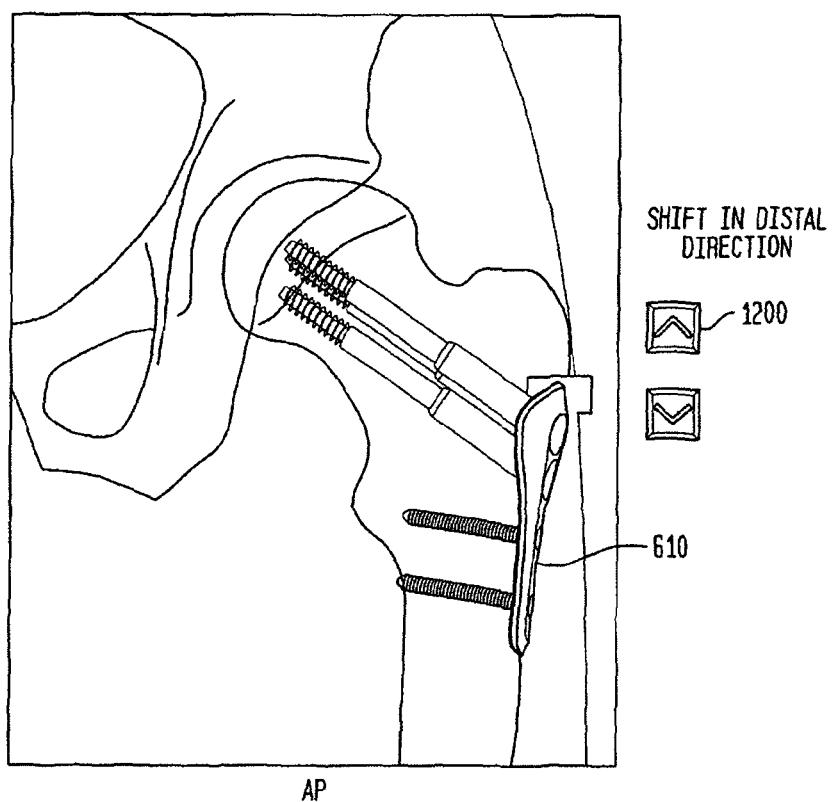
FIG. 12A shows a step of automatically adjusting the proposed position of the intracapsular plate in the distal direction.
Figure 12B:
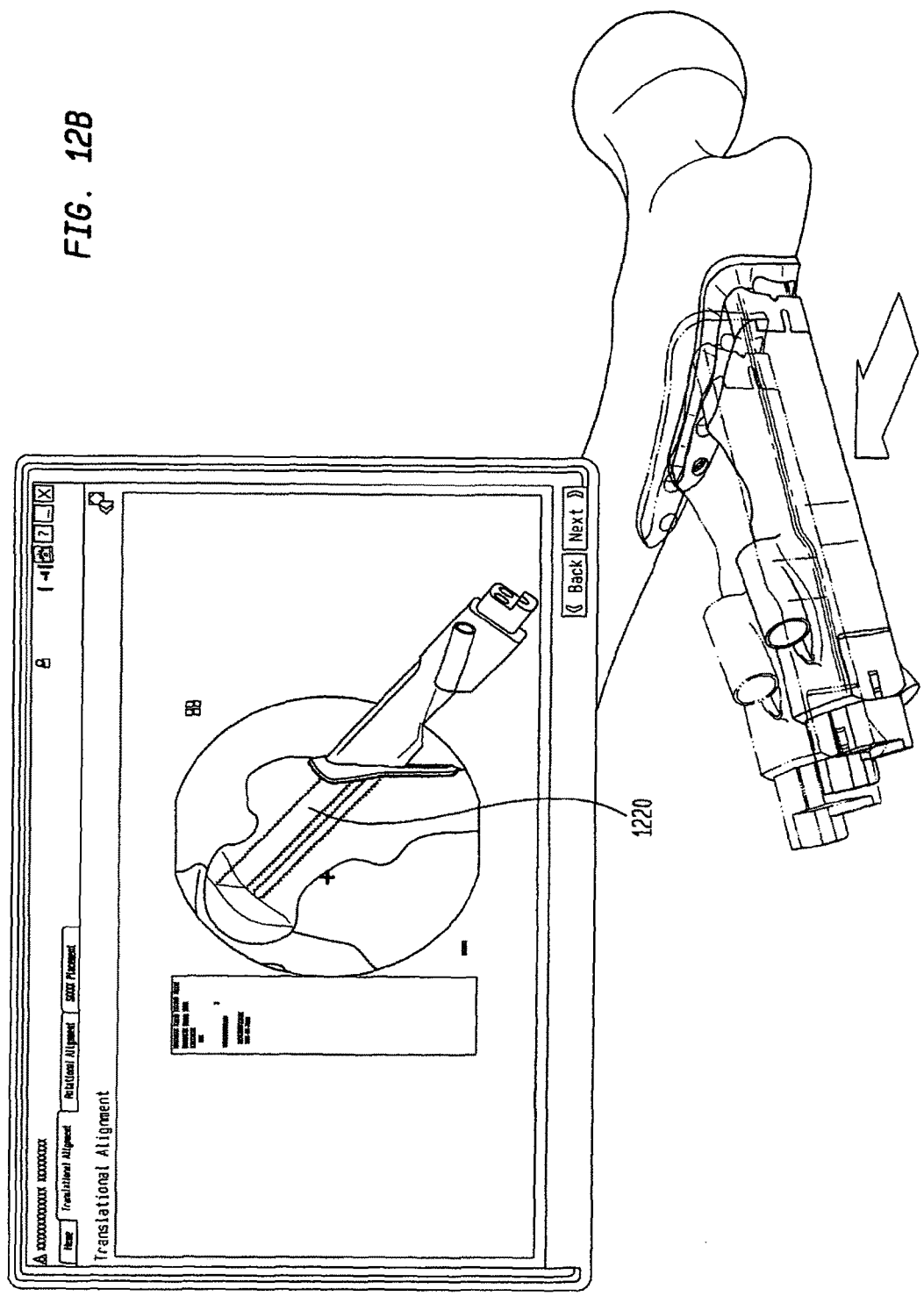
FIG. 12B shows a step of automatically adjusting the proposed position of the intracapsular plate in the distal direction.

The visualization also allows the surgeon to manually adjust the position of the actual ICP if better alignment is considered necessary. For example, FIG. 12A shows a proposed adjustment of the ICP 510 in the distal direction, as seen from the AP two dimensional image. More specifically, as can be also seen from FIG. 12B, the display may also include zones that indicate preferable translational adjustment of the implant relative to its current location. For example, an acceptance zone 1220 (e.g., using colors) may be used to indicate a more preferable location. Thus, if the screws are located outside this area distally, the surgeon may manually adjust the plate at S55 and view an updated visualization by returning to step S52.

FIGS. 13A and 13B show how adjustment of the ICP 610 by external rotation 1300 can be achieved. In particular, similar to the case of translational adjustment, if the surgeon believes that the implant is not aligned properly, he/she may adjust arrows 1300 to visualize how the implant is aligned if rotated. As can be also seen from FIG. 13B, an acceptance zone 1340 may be used to show how rotation would change the location of the screws from a preferred position. As is also shown in FIG. 13B, rotational movement is preferably performed after the location along the femur neck has been satisfactorily determined. In this way, the reference body 604 may fixed to the bone using a pin 1326. This pin 1326 may then be used with teethed gear mechanism 1330 to more precisely rotate the implant as shown.

As discussed above, the present invention is reactive in that the system reacts to the surgeon in lieu of requiring the surgeon to take action or interact with the computer or system. As such, if the surgeon decides that the implant is properly aligned, he/she can then decide to secure the implant and complete the procedure. This minimizes disruptions in current OR workflow and allows the surgeon to use his/her judgment as part of the workflow. In contrast, conventional approaches tend to disrupt the OR workflow by requiring the surgeon to interact with the CAS. This typically lengthens the surgical procedure and requires more in the way of equipment, both of which increase the cost of surgical procedures.

Figure 15:
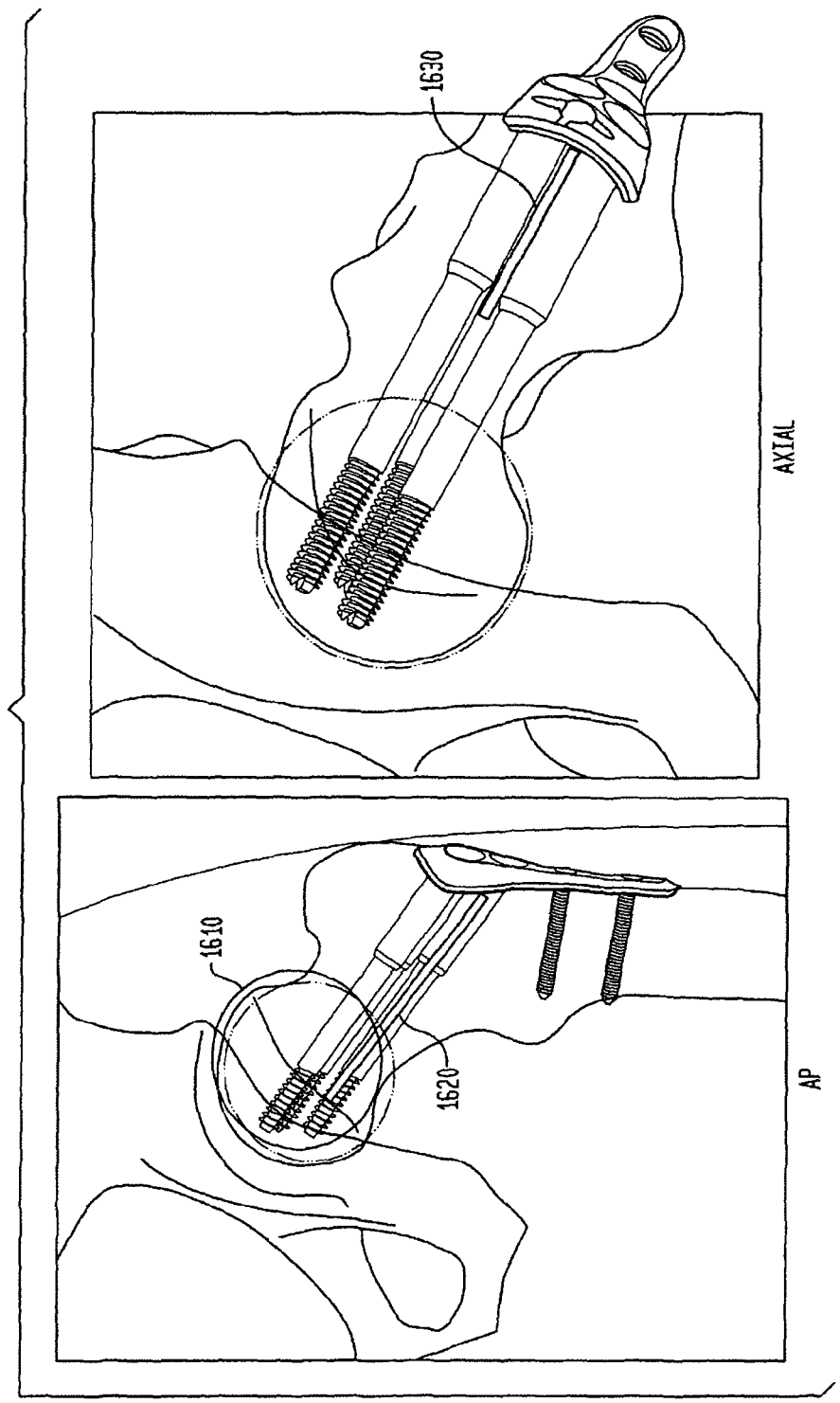
FIG. 15 shows automatic detection of the insertion of K-wires and detecting movement of the femur head to ensure a reactive behavior.

Upon completion of the steps outlined above in relation to step S408, the procedure continues to step S424, where the implant may be affixed to the region of interest. Additional fluoroshots may be taken during or after step S424 to verify reduction of the fracture and the position of the ICP and K-wires or screws. For example, FIG. 15 shows the insertion of K-wires 1620, 1630 and a detected movement of the femur head 1610. Ideally, the system will detect such movement and propose a corrective action such as new screw lengths. If necessary, further re-positioning of the implant and reduction of the fracture can be performed as discussed above.

As discussed above, Kirshner wires (K-wires) can be inserted through openings in the reference body 604. More specifically, as shown in FIG. 15, a first K-wire (1630 may be inserted to fix the plate to the bone. (A second K-wire 1620 may also be inserted through the fracture.) Screws can then be inserted to compress the fracture (S424). The screws may be self-tapping or be inserted through drilled holes. The invention preferably includes image processing software that is based on edge detection to detect any insertion and bending of the screws or K-wires. Such software may comprise a component or routine in a set of instructions that carry out the method described above. The ICP has threaded screw holes so that the screw position/angle relative to the plate is fixed. The K-wires may be removed before or after the screws have been inserted.

Figure 14:
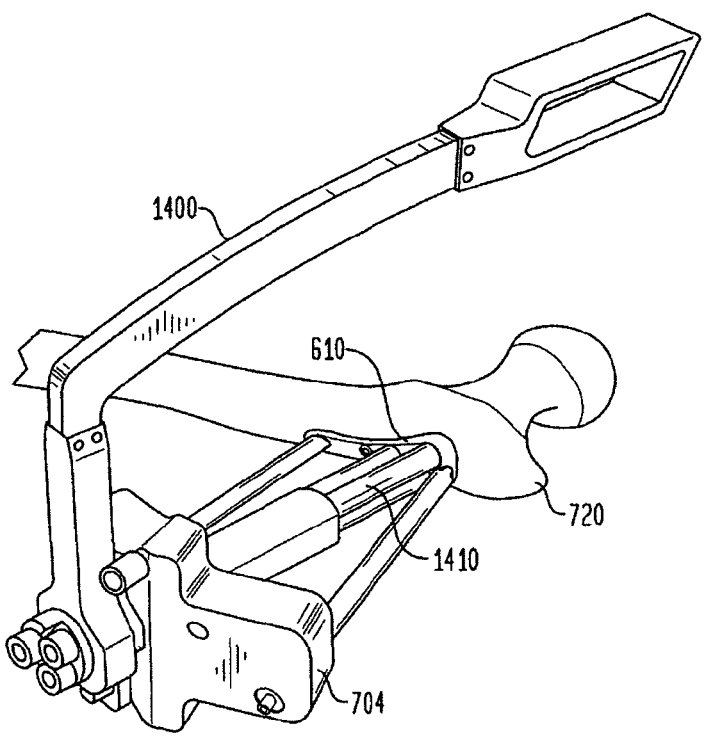
FIG. 14 shows the re-positioning and fixation of the intracapsular plate based on the proposed position.

Alternatively, an aiming apparatus with scaling in combination with an oblong-shaped hole (wherein a K-Wire may be inserted) may be directly attached to the ICP and used to assist in the mounting and any further adjustment deemed necessary by the surgeon. FIG. 14 shows repositioning using a prior art one-shot apparatus 1400; which is preferably replaced by the reference body 604 and other attachments 1326, 1330 discussed above.

Turning now to FIGS. 16A-16H, there is shown an alternative use of the methods described above in accordance with a further aspect of the present invention. As will be discussed in detail, these figures show insertion of a locking nail 1654, which is used as part of a hip fracture repair system. In particular, and with reference FIG. 16A, the procedure begins with insertion of the nail 1654 into the femur 1658. As is also shown, the nail 1654 is attached to an instrument or aiming device 1660. The aiming device is preferably equipped with a plurality of fiducial markers, e.g., four or more, that act as a reference body that is detectable by the imaging system. In accordance with the methods previously described, at this initial state of the procedure, the surgeon obtains fluoroshots along a first dimension. For example, a fluoroshot may be obtained along the anterior-posterior axis of the patient or at any other angle the surgeon deems suitable.

Figure 16A:
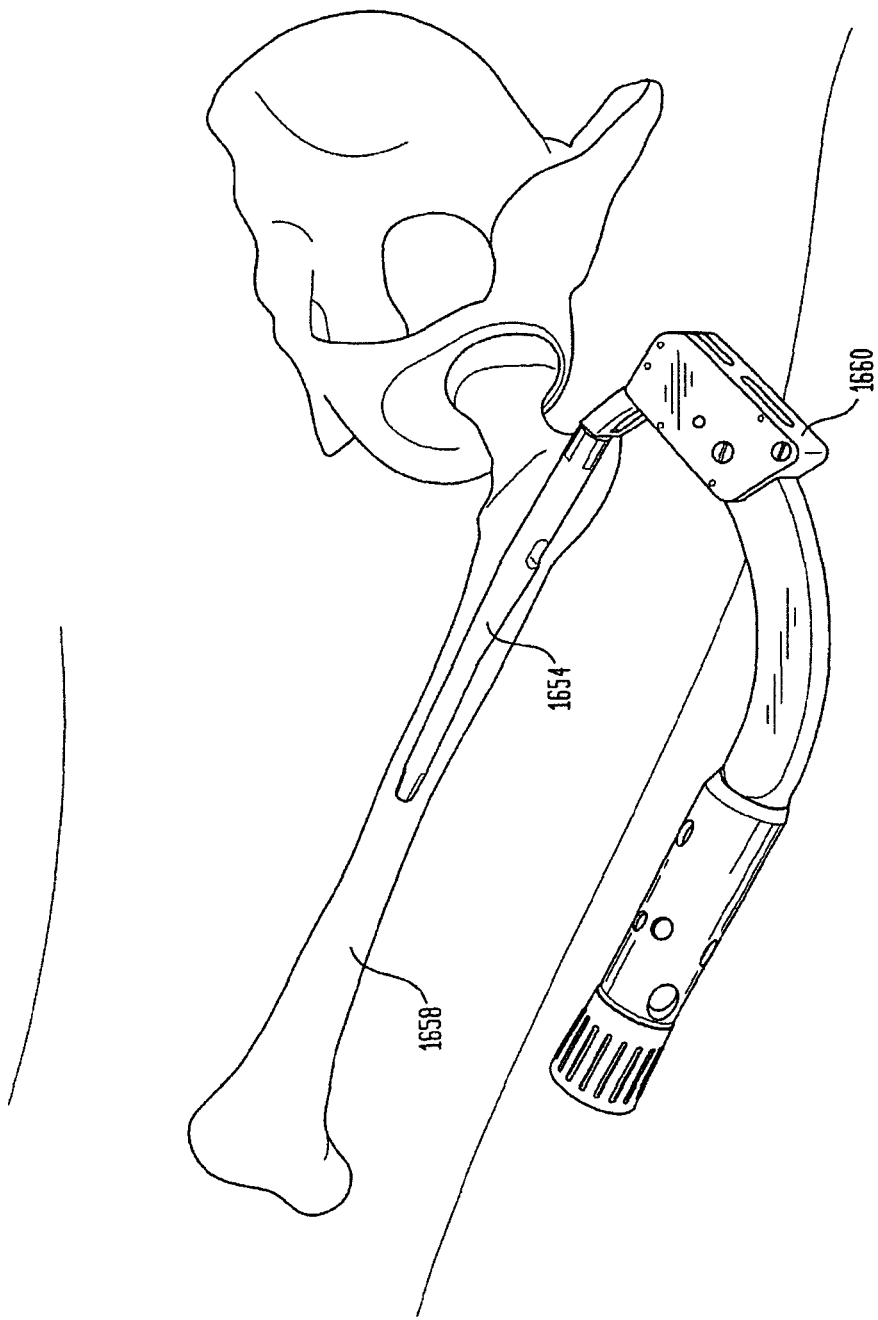
Figure 16B:
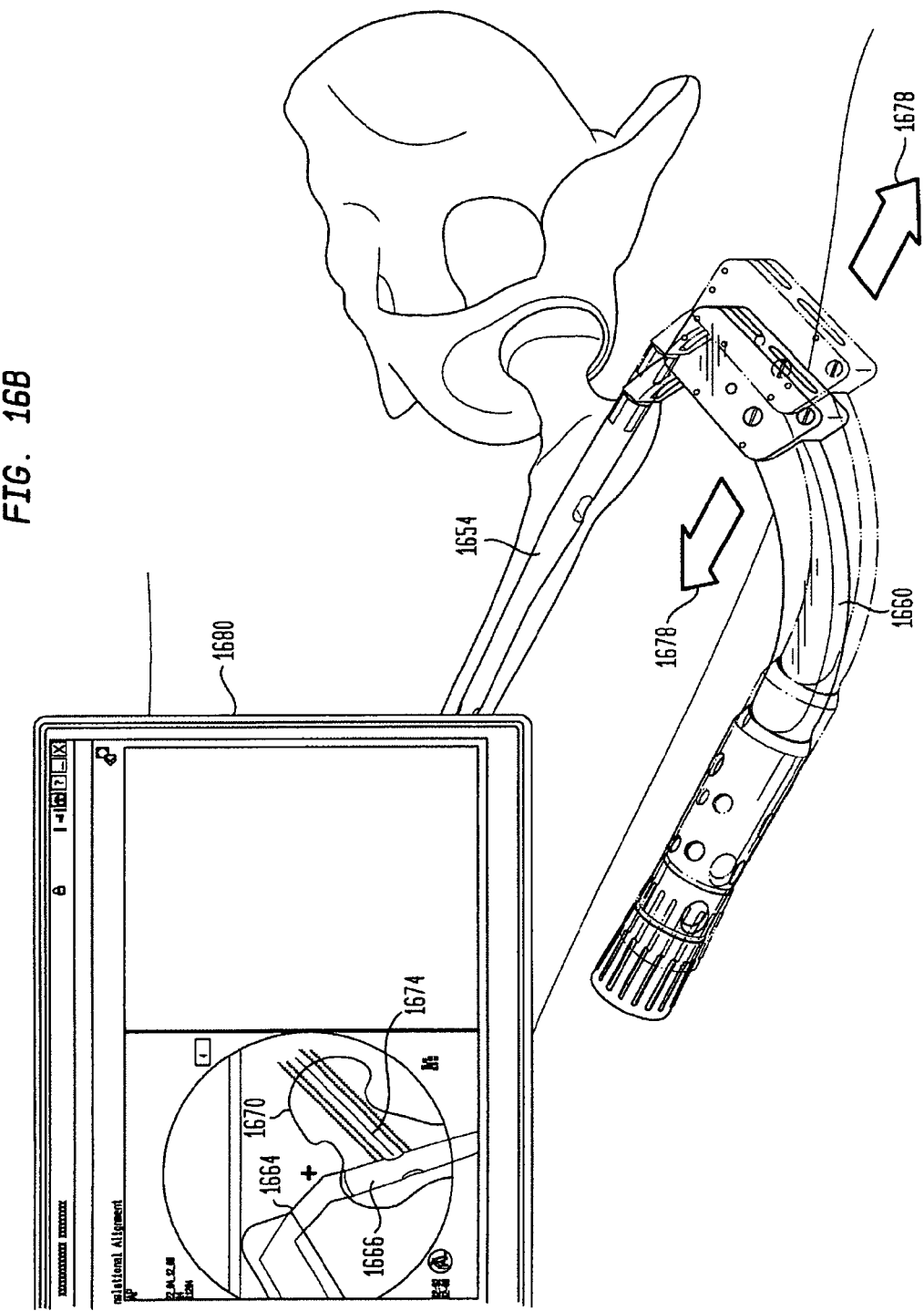

As is shown in FIG. 16B, if the shot is taken along the anterior-posterior direction, the computer 120 detects calculates the position of the reference body and instrument 1660, and displays a virtual nail 1666 in relation to the region of interest 1670. In addition, the display includes a projection 1674 of the location of a screw that will be used to secure the nail 1654 within the femoral head or region of interest 1670. As is also depicted in FIG. 16B, if the projected path 1674 of the screw is determined by the surgeon to require some adjustment, the surgeon may make a translational adjustment 1678 of the nail within the femur 1658. After making the translational adjustment 1678, the surgeon then, preferably, takes an additional fluoroshot to confirm that the adjustment moved the nail 1654 into a more desirable position using they display 1680 similar to that shown.

Once the surgeon is satisfied with translational alignment of the nail 1654, he may then use the system to rotationally align the nail as is shown in FIG. 16C. In particular, the surgeon would take a fluoroshot at a different angle, such as along a hip lateral direction to obtain the image 1684 shown in FIG. 16C. Using this image, the surgeon may rotate the nail 1654 into a more desirable position and take additional fluoroshots to confirm the adjustment.

Figure 16D:
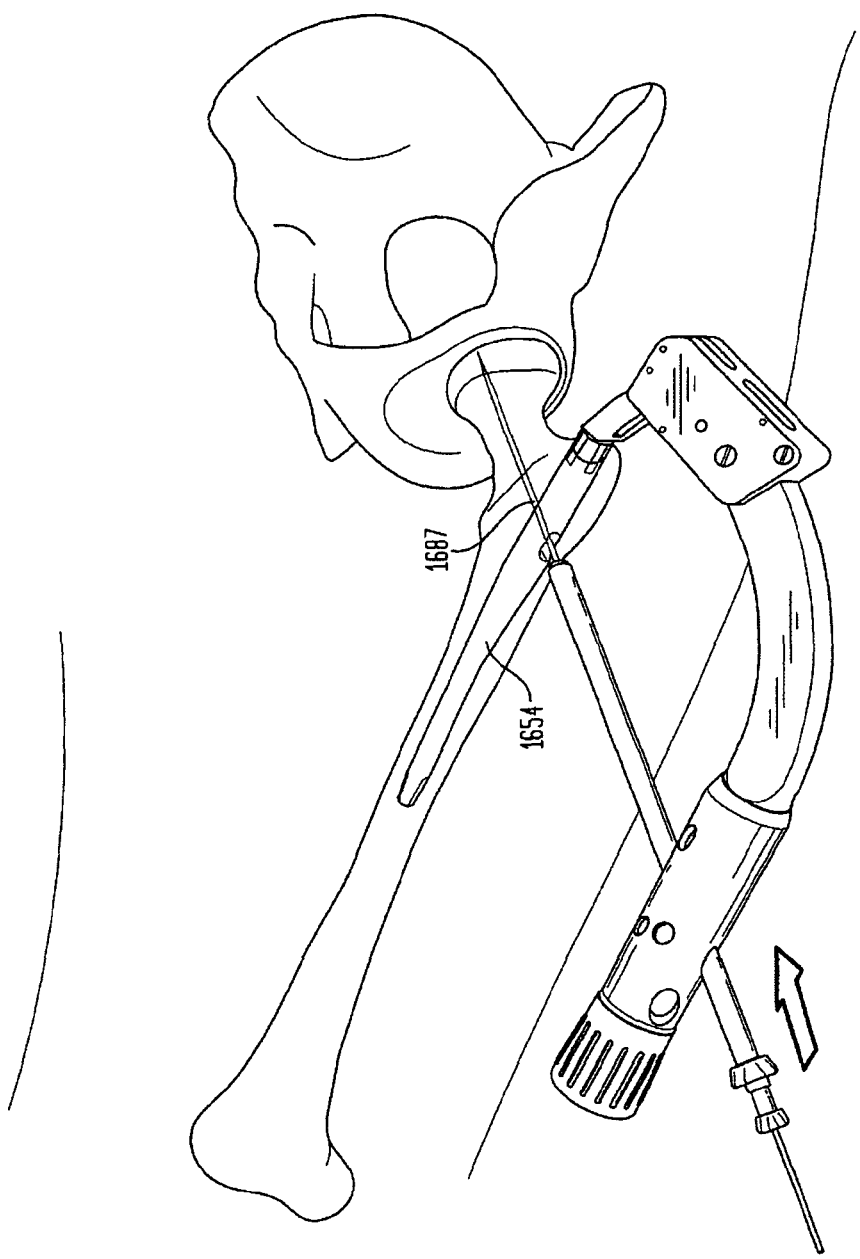
Figure 16E:
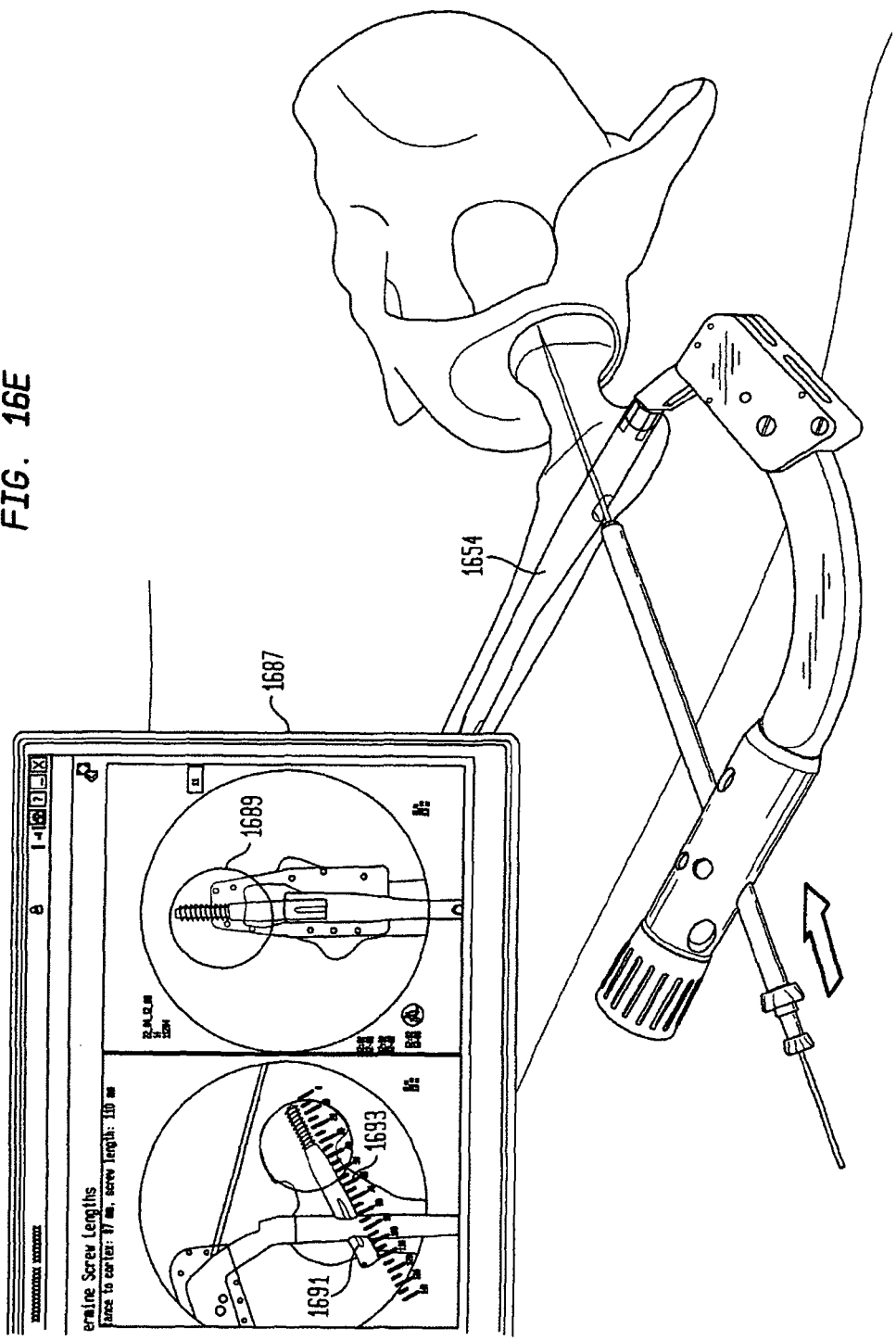

Once the surgeon determines that the nail 1654 is suitably aligned, he may then insert a K-wire 1687 as is shown in FIG. 16D. With the K-wire inserted, two or more two-dimensional images may be obtained with the fluoroscope, as described above. Using these two or more images, the system is then able to determine the appropriate screw lengths, as is shown in FIG. 16E. In particular, the two-dimensional images are used to create an object that models the region of interest, in this case, the femoral head. More specifically, where the region of interest is the femoral head, the computer 120 uses these two-dimensional images to create a sphere 1689 and superimposes within the sphere the location and lengths of screws that may be used to attach the nail 1654. As is shown in FIG. 16E, the display includes a virtual screw 1691 along with tick marks 1693 that indicate the length of the screw just within the sphere 1689 and out through an opening in the nail 1654.

Figure 16F:
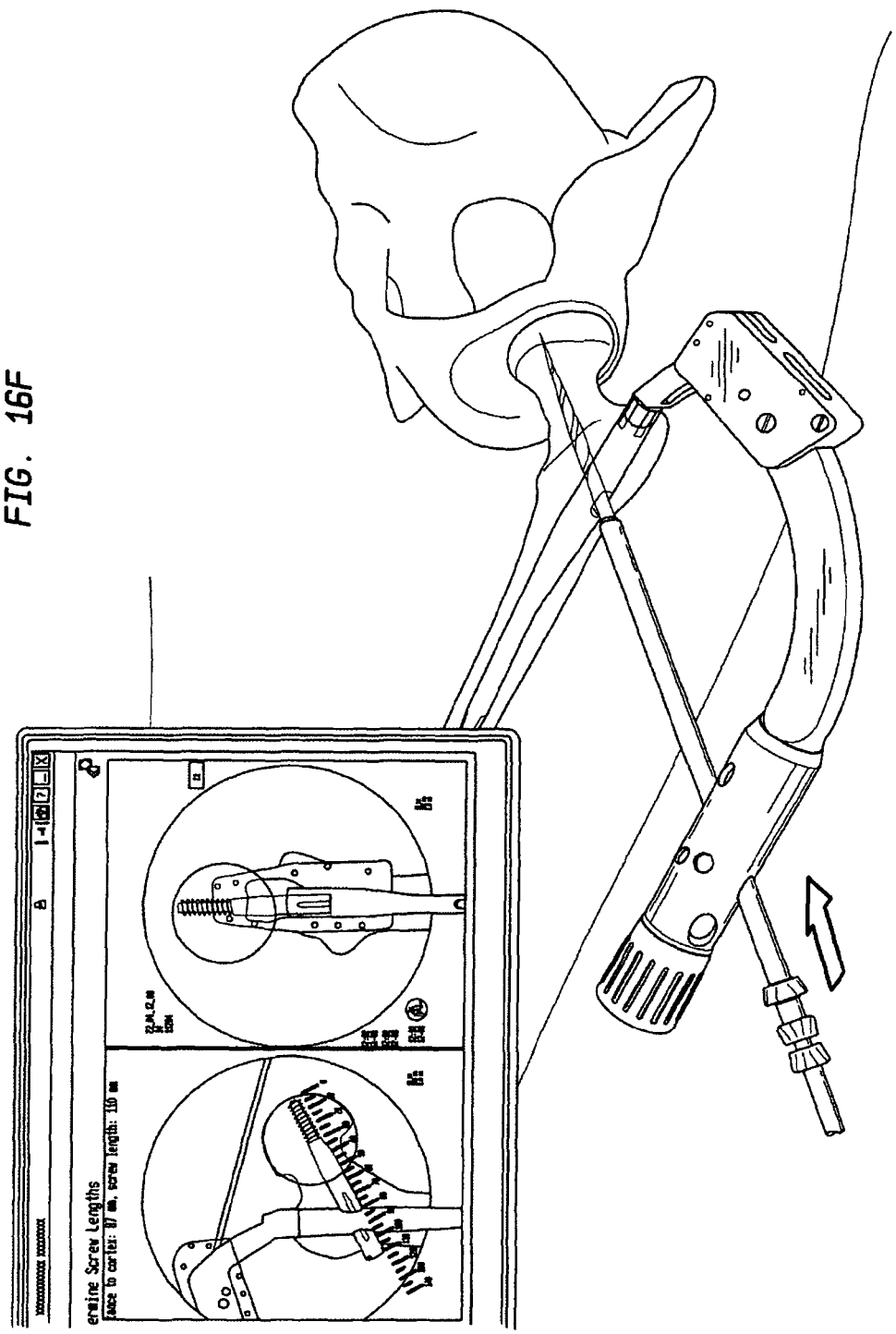
Figure 16G:
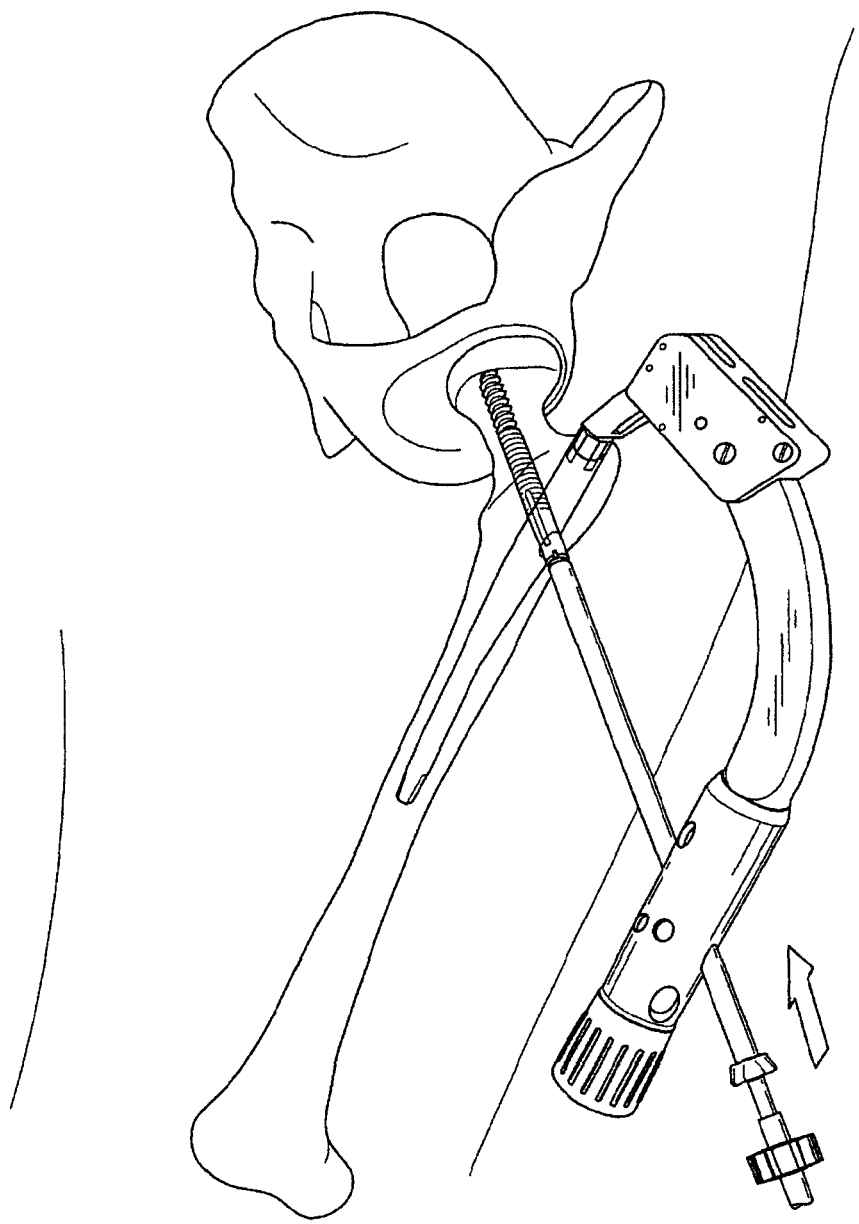
Figure 16H:
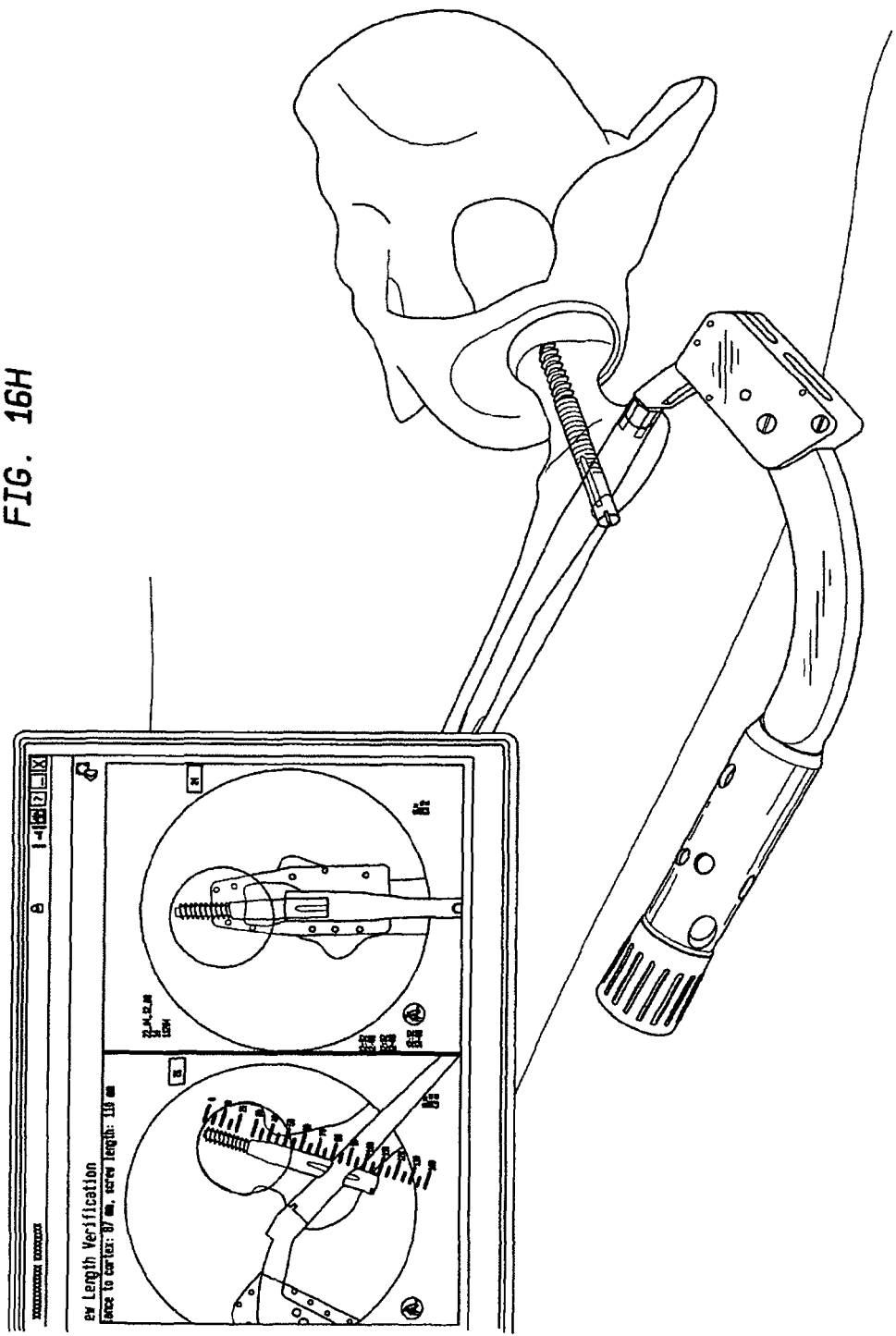

Based on the tick marks 1693 shown in FIG. 16E, the surgeon may then select an appropriate screw of desirable length to affix the nail 1654. Once the screw is selected, it is then inserted as is shown in FIGS. 16F and 16G. As is also described above, once a screw is in place, additional images may be taken to verify that the length of the screw secure the device without protruding outside the region of interest as a result of the forces that were applied during the affixation procedure, as is illustrated in FIG. 16H.

The image processing performed by the invention includes: anatomic feature detection and segmentation; position detection of the reference body; generation of 3D information from 2D images; registration, rendering and display of 3D information on 2D images; and calculation of the optimal position of the implant. In addition, in another aspect, the system may propose an appropriate length for each screw.

As discussed above, at least two 2D images containing the reference body are required by the invention to provide 3D information. These images should be taken at different angles (preferably near a 90 degree angle). Additional 2D images can also be used to provide information. The images can be registered to one another by detecting distinctive anatomic features in the images and/or by using the reference body. The reference body (which occurs in each image) can be used to precisely register the images in three dimensions. The reference body can also be helpful in automatically detecting these anatomic structures for segmentation (e.g. detecting feature borders). The relative position of specific anatomical structures to the position of the reference body may also be estimated based on general bone shape statistics and on patient data (e.g. size, gender, age). This relative position may be used as a starting point for the segmentation algorithms. Once the anatomic structures have been segmented, the image processing software can correlate the structures from different images to generate 3D information.

Various three-dimensional reconstruction algorithms can be used to generate this information. Typically, the algorithms will approximate the segmented anatomic features with geometric shapes (e.g., a circle). The geometric shapes are then matched/registered to their known relative positions in the 2D images. These shapes are then projected into 3D space to form, for example, a sphere or cylinder. The invention may initially select a typical 3D Shape for an anatomic region from a database and match it with the image by zooming, rotating, and/or translating the shape. The shape may also be altered, such as with a morphing algorithm, for a better match. In fact, pre-operative images may be taken of the same anatomic region to better determine the actual shape of various features.

Because the reference body is located within each image and is attached to an anatomic region (e.g. a bone), movement of the patient during surgery is not a problem in accordance with an aspect of the present invention. This is because the system can use the location of the reference body to register different fluoroscope images (independent of the image content) and generate a low artifact real 3D image using 3D reconstruction algorithms. This aspect of the invention to precisely register the images significantly reduces artifacts due to patient movement during surgery.

Preoperative planning may be performed by taking pre-operative images similar to the intra-operative images. This pre-operative planning can be used to determine the optimal sub-implant positioning which may then be checked against the intra-operative positioning. Such pre-operative images could be processed using different algorithms which are too time consuming to use during surgery or could be segmented and matched manually.

As discussed above, the invention may also provide a reactive workflow by automatically detecting the status of an operation and thus knowing the next operative steps to be performed. In this manner, the invention might provide suggestions to the surgeon. For example, the invention may suggest a specific type, size, or shape of a best-fit implant based on the detected geometry of a fracture. Moreover, the invention could modify a previous suggestion based on additional information determined during the surgery.

Additional distinctive aspects of the invention include that the stereo-tactic device is implanted in the body. In addition, the invention uses 2D images (e.g. fluoroscopic x-rays) to generate 3D information. The reference plate (ICP) is contoured to match the surface contour of the bone to restrict the degrees of freedom for adjustments. The reference plate (ICP) is also threaded so relative screw position is known. The invention calculates and proposes reference plate position, sphere position, screw position and lengths.

Advantages of the invention include that it reduces the surgery time for insertion of an implant, requires almost no interaction between the surgeon and the system, provides three-dimensional information on important regions, requires little change to operating room procedures, and is cheaper than current tracking based navigation. Additional features of the invention include that it takes into account any bending of Kirshner wires (K-wires) through automatic detection, calculates and displays any dislocation of the femur head during implantation, and calculates the screw lengths.

Although the invention herein has been described with reference to an ICP procedure, it is to be understood that this embodiment is merely illustrative of the principles and applications of the present invention. It is therefore to be understood that numerous modifications may be made to the illustrative embodiment and that other arrangements may be devised without departing from the spirit and scope of the present invention.

The invention claimed is:

1. A method for operating a computer assisted surgical system for implanting a medical device having a main implant and a sub-implant, and being represented by a virtual medical device, the method comprising:
   implanting the main implant coupled to a reference body having at least four fiducial markers arranged in a predetermined three-dimensional pattern, the reference body being in a known spatial relationship with the main implant, the fiducial markers detectable by a fluoroscopic imaging system;
   fluoroscopically imaging a region of interest and the main implant associated with the reference body to produce first and second two-dimensional fluoroscopic images, the first and second fluoroscopic images representing the position of the main implant proximate the region of interest of a portion of an anatomy of a subject at a first angle to obtain the first two-dimensional image and at a second angle to obtain the second two dimensional image to produce three dimensional information associated with the region of interest;
   detecting the presence of the reference body having the at least four fiducial markers in the first and second images;
   repositioning the main implant and reference body;
   processing one additional two-dimensional fluoroscopic image with respect to the repositioned reference body fiducial markers by identifying and registering the fiducial markers of the reference body in the one additional two-dimensional fluoroscopic image, to produce location information of the main implant superimposed over the region of interest, wherein the location information of the main implant is determined based solely on the location of the fiducial markers in the one additional fluoroscopic image;
   associating, based on the location information of the main implant superimposed over the region of interest, the not yet implanted sub-implant with the region of interest in a predetermined relationship relative to the reference body representing the main implant, the main implant and the sub-implant having a fixed predefined spatial relationship to one another upon implantation; and
   displaying the association of the main implant, the not yet implanted sub-implant and the region of interest as an image showing the virtual medical device superimposed over the region of interest such that the not yet implanted sub-implant is displayed as having a virtual fixed predefined spatial relationship to the main implant that is the same as the fixed predefined spatial relationship between the main implant and the sub-implant upon implantation.

2. The method of claim 1, wherein the reference body is attachable to one of the main implant and a targeting device, wherein the reference body has a characteristic two-dimensional projection.

3. The method of claim 1, further comprising:
   associating, based on the three dimensional information of the main implant superimposed over the region of interest, the not yet implanted sub-implant with the region of interest in a predetermined relationship relative to the reference body representing the main implant; and
   displaying the association of the main implant, the not yet implanted sub-implant and the region of interest as an image showing the virtual medical device superimposed over the region of interest.

4. The method of claim 3, wherein the region of interest comprises a femoral head, the two dimensional images comprise anterior-to-posterior and axial images of the femoral region and estimating comprises forming an outline of the femoral head on the anterior-to-posterior and axial images.

5. The method of claim 1, further comprising determining a length of the not yet implanted sub-implant for selecting the required sub-implant.

6. The method of claim 1, further comprising detecting the presence of the reference body based on the fiducial markers.

7. The method of claim 1, wherein processing further comprises estimating the contours of the region of interest in two dimensions based on the one two-dimensional image.

8. The method of claim 7, wherein processing further comprises forming a three dimensional image associated with the region of interest based on the estimation.

9. The method of claim 1, further comprising adjusting the position of the main implant and repeating the steps of imaging, processing, associating and displaying.

10. A computer assisted surgical system, comprising:
an apparatus for imaging a region of interest of a portion of an anatomy of a subject and a medical device having an implanted main implant and a sub-implant being represented by a virtual medical device;
a memory containing executable instructions; and
a processor programmed using the instructions to:
mount a reference body having a three-dimensional pattern of at least four radiopaque markers therein onto the main implant in a known relationship thereto;
obtain a plurality of two-dimensional images of the region of interest with the main implant associated with the reference body, the image representing the position of the main implant proximate the region of interest of a portion of an anatomy of a subject at a first and second angle;
process the two-dimensional images to produce three dimensional information of the region of interest and the reference body with respect to the reference body radiopaque markers to produce information of the main implant superimposed over the region of interest, wherein the information includes the actual spatial position of the main implant and the reference body radiopaque markers and registration of the reference body in the images;
associate, based on the position of the main implant superimposed over the region of interest and an image of the reference body and radiopaque markers, the not yet implanted sub-implant with the region of interest in a predetermined relationship relative to the reference body representing the main implant, the main implant and the sub-implant having a fixed predefined spatial relationship to one another upon implantation; and
generate a display signal associated with the main implant, the not yet implanted sub-implant and the region of interest as an image showing the virtual medical device superimposed over the region of interest such that the not yet implanted sub-implant is displayed as having a virtual fixed predefined spatial relationship to the main implant that is the same as the fixed predefined spatial relationship between the main implant and the sub-implant upon implantation.

11. The computer assisted surgical system of claim 10, wherein the apparatus comprises a fluoroscope.

12. The computer assisted surgical system of claim 10, wherein the associated sub-implant provides an estimate of the location of the main implant and one or more sub-implants within the region of interest.

13. The computer assisted surgical system of claim 10, wherein the processor processes the one or more two-dimensional images by outlining the contours of the region of interest in two dimensions and creates a three dimensional object representing the region of interest.

14. The computer assisted surgical system of claim 13, wherein the three dimensional object comprises a sphere.

15. The computer assisted surgical system of claim 13, wherein the three dimensional object is derived from a database and based on age and gender of the patient.

16. The computer assisted surgical system of claim 13, wherein the three dimensional object is determined based on landmarks associated with the region of interest.

17. The computer assisted surgical system of claim 10, wherein the system is adapted to take into account bending of Kirschner wires through automatic detection.

18. The computer assisted surgical system of claim 10, wherein the system is adapted for calculating and displaying a dislocation of a femur head during implantation.

19. The computer assisted surgical system of claim 10, wherein the system is adapted for calculating required sub-implant lengths.

20. The computer assisted surgical system of claim 10, wherein the system is adapted for automatically detecting a status of an operation and determining next operative steps to be performed so as to provide a reactive system.

21. The computer assisted surgical system of claim 10, wherein the system is adapted to provide suggestions to the surgeon with respect to at least one out of a group, the group consisting of a specific type, a specific size, and a shape of a best-fit implant based on a detected geometry of a fracture.

22. The computer assisted surgical system of claim 21, wherein the system is adapted to modify a previous suggestion based on additional information determined during the surgery.

23. A method for operating a computer assisted surgical system for implanting a medical device having a main implant and a sub-implant, and being represented on a monitor by a virtual main implant and a virtual sub-implant, the method comprising:
imaging a region of interest with an implanted actual main implant associated with a reference body in a known spatial relationship, the reference body including at least four radiopaque fiducial markers mounted on two spaced planes, the imaging representing the position of the actual main implant proximate the region of interest of a portion of an anatomy of a subject at a first angle and a second angle to obtain first and second two-dimensional images;
processing a single additional two-dimensional image with respect to the reference body by identifying and registering the reference body in the two-dimensional image using the fiducial markers to produce three dimensional information of the reference and main virtual implant superimposed over the region of interest, wherein the information of the virtual main implant include an actual position of the actual implant;
associating, based on the information of the virtual main implant superimposed over the region of interest, the virtual sub-implant to be implanted with the region of interest in a predetermined relationship relative to the reference body representing the actual main implant, the actual main implant and the actual sub-implant having a fixed predefined spatial relationship to one another upon implantation; and
displaying the association of the virtual main implant, the virtual sub-implant to be implanted and the region of interest as an image showing the virtual main implant and virtual sub-implant superimposed over the region of interest such that the sub-implant is displayed as having a virtual fixed predefined spatial relationship to the main implant that is the same as the fixed predefined spatial relationship between the main implant and the sub-implant upon implantation, and virtually realigning the main implant and sub-implant until a satisfactory position is reached including the location of the reference body fiducial markers and thereafter implanting the actual sub-implant in the satisfactory position based on the location of the fiducial markers in additional images.

24. The method of claim 23, wherein the reference body is attachable to one of the actual main implant and a targeting device, wherein the fiducial markers of the reference body have a characteristic two-dimensional projection.

* * * * *